(12) United States Patent
Raines

(10) Patent No.: US 12,280,262 B2
(45) Date of Patent: Apr. 22, 2025

(54) SLIP RING ANCHOR

(71) Applicant: Advanced Neuromodulation Systems, Inc., Plano, TX (US)

(72) Inventor: Aaron Raines, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 939 days.

(21) Appl. No.: 17/322,785

(22) Filed: May 17, 2021

(65) Prior Publication Data

US 2022/0161041 A1  May 26, 2022

Related U.S. Application Data

(60) Provisional application No. 63/117,736, filed on Nov. 24, 2020.

(51) Int. Cl.
| | | |
|---|---|---|
| *A61N 1/375* | (2006.01) | |
| *A61N 1/05* | (2006.01) | |
| *A61M 25/02* | (2006.01) | |

(52) U.S. Cl.
CPC ....... *A61N 1/37518* (2017.08); *A61N 1/0539* (2013.01); *A61N 1/0558* (2013.01); *A61N 1/059* (2013.01); *A61M 2025/0293* (2013.01)

(58) Field of Classification Search
CPC ........... A61M 2025/0293; A61N 1/059; A61N 1/0558; A61N 1/0539; A61N 1/37518; A61N 1/057; A61N 2001/0582
See application file for complete search history.

(56) References Cited

U.S. PATENT DOCUMENTS

| | | |
|---|---|---|
| 4,516,584 A | 5/1985 | Garcia |
| 8,140,172 B1 | 3/2012 | Jones et al. |
| 9,026,227 B2 | 5/2015 | Daglow |
| 2009/0125058 A1 | 5/2009 | Bodner et al. |
| 2009/0125061 A1 | 5/2009 | Rivard et al. |
| 2011/0009935 A1 | 1/2011 | Kane et al. |

(Continued)

OTHER PUBLICATIONS

Patent Cooperation Treaty, International Search Report and Written Opinion issued for PCT Application No. PCT/US2021/060544, dated Feb. 23, 2022, 12 pages.

(Continued)

*Primary Examiner* — Chelsea E Stinson
*Assistant Examiner* — Nelson Louis Alvarado, Jr.
(74) *Attorney, Agent, or Firm* — Norton Rose Fulbright US LLP

(57) ABSTRACT

Systems and methods which provide a slip ring anchor configuration in which an anchor body includes inelastic members and a fluted elastomeric casing operable in cooperation to impart a radial compressive force to a corresponding lead body are described. A slip ring anchor body may comprise a plurality of inelastic members alternately disposed in flutes of a fluted elastomeric casing portion of the anchor body. The fluted elastomeric casing may form an anchor lumen through which a lead body may be inserted. Once a slip ring anchor is disposed at a desired position axially along the lead body, manipulation of one or more slip rings may be used to cause a radial compressive force to be imparted upon the lead body. A slip ring actuator tool may be used to manipulate a slip ring between unlocked and locked positions.

36 Claims, 18 Drawing Sheets

(56) References Cited

U.S. PATENT DOCUMENTS

| | | |
|---|---|---|
| 2012/0232626 A1 | 9/2012 | Daglow |
| 2012/0232627 A1 | 9/2012 | Swoyer et al. |
| 2012/0330355 A1* | 12/2012 | Finley ................ A61B 17/0401 |
| | | 606/232 |
| 2013/0261719 A1 | 10/2013 | Sage |
| 2017/0043157 A1* | 2/2017 | Barner ................ A61N 1/0558 |

OTHER PUBLICATIONS

European Patent Office, Communication, Extended Search Report issued for European Patent Application No. 21899024.0, dated Sep. 16, 2024, 9 pages.

* cited by examiner

SLIP RING ANCHOR

CROSS-REFERENCE TO RELATED APPLICATIONS

The present application claims the benefit of U.S. Provisional Patent Application No. 63/117,736, entitled "SLIP RING ANCHOR FOR MEDICAL DEVICE LEADS," filed Nov. 24, 2020 the disclosure of which is hereby incorporated by reference herein in its entirety as if fully set forth below and for all applicable purposes.

TECHNICAL FIELD

The present invention relates to medical device leads and, more particularly, to anchors for leads used in the medical field.

BACKGROUND OF THE INVENTION

Implantable medical devices are used for a wide variety of medical conditions. For example, a number of implantable medical devices have been commercially distributed that allow various medical agents to be controllably infused after implantation of the respective device within a patient. Such implantable medical devices may be used for the infusion of insulin, opiates, antispasmodic drugs, intrahepatic chemotherapy agents, and other therapeutic agents in a number of countries subject to the regulatory requirements of those countries. As another example, a number of implantable medical devices have been commercially distributed that allow electrical pulses or signals to be controllably delivered to a targeted tissue or nerves after implantation of the respective device within a patient. Such implantable medical devices may be used for cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression.

Implantable infusion devices typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes. To deliver the infusate from the reservoir, a lead in the form of a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient).

Implantable electrical stimulation devices generally include an implanted pulse generator that generates electrical pulses or signals that are transmitted to a targeted tissue or nerves through a therapy delivery element, such as a lead with electrodes. Controlled placement of the therapy delivery element is required for improved therapeutic efficacy or reduced side effects. Retaining the implanted therapy delivery element in the desired location also creates difficulties because the location may change over time as the patient moves.

Whether in a stimulation, sensing or element delivery capacity, leads are (e.g., catheter or lead having electrodes) commonly implanted along peripheral nerves, within the epidural or intrathecal space of the spinal column, and around the heart, brain, or other organs or tissue of a patient. For example, leads are often inserted such that the lead ends are adjusted precisely within the an area of placement so as to maintain an orientation, position, spacing, etc. with respect to surrounding tissue to facilitate effective treatment of one or more indications. Current lead designs, however, are often prone to movement (e.g., axially, radially and/or longitudinally) after insertion if steps are not take to control such movement. Typically, some mechanism is employed to anchor the leads so that the therapeutic agent (e.g., infusate or electrical signal) will continue to be delivered to the appropriate site. Accordingly, various forms of anchoring structures have been utilized to discourage movement of the lead and/or the electrodes, such as to facilitate satisfactorily long functional survival time of the lead, to avoid the reprogramming or replacement of the lead to restore effective therapy, etc.

Most anchor structures for use with implantable medical device leads are either slid over the lead or clamped over the lead. In some examples, the anchor structure is secured to the lead at the same time the anchor is sutured to the fascia. For example, an anchor may be slid onto the proximal end of a lead body while maintaining the position of the lead within the body of the patient. The anchor may be secured to the lead by tying ligatures around grooves in the anchor when the anchor is sutured to the fascia or other tissue (e.g., supraspinous ligament). Existing techniques for securing anchors to the lead body can be problematic. For example, the force needed to secure the anchor to the lead is usually more than the force needed to secure the anchor to the fascia, which can lead to the lead moving axially within the anchor.

Some anchor designs attempt to address the potential for the lead moving axially within the anchor by implementing a crimping technique. For example, the anchor may be crimped onto the lead body to provide a tight friction interface between the anchor and the lead. Such a crimped interface, however, often creates sharp concentrated shear forces on the lead that can be stress points that can lead to lead factures in some cases. Additionally or alternatively, if moved, crimped anchors can cause lead factures due to previous clamped areas being stressed as a result of normal body motions.

BRIEF SUMMARY OF THE INVENTION

The present invention is directed to systems and methods which provide a slip ring anchor configuration in which an anchor body includes inelastic members and a fluted elastomeric casing operable in cooperation to impart a radial compressive force to a corresponding lead body. For example, in accordance with some embodiments of the invention, a slip ring anchor body may comprise a plurality of inelastic members alternately disposed (e.g., interleaved) in the flutes of a fluted elastomeric casing portion of the anchor body. The fluted elastomeric casing may form an inner diameter (e.g., anchor lumen) through which a lead body may be inserted. Once a slip ring anchor of this configuration is disposed at a desired position axially along the lead body, manipulation of one or more slip rings may be used to cause a radial compressive force to be imparted upon the lead body by the slip ring anchor. A slip ring actuator tool of embodiments may be used to manipulate a slip ring between unlocked and locked positions with respect to a slip ring anchor, such as for affixing the slip ring anchor at a desired position on a lead body through application of a radial compressive force, disengaging the radial compressive force for removal or repositioning of the slip ring anchor, etc.

Slip ring anchors configured according to concepts of the present invention provide a tight friction interface between the anchor and the lead without introducing sharp concentrated shear forces on the lead that can be stress points. For example, slip ring anchors of embodiments are configured to distribute compressive forces substantially equally around the lead body, such as by the slip ring anchor squeezing relatively consistently 360° around a portion of the anchor comprising a fluted elastomeric casing with alternately disposed inelastic members compressed by a slip ring. Further, slip ring anchors of embodiments are configured to avoid sharp shear stresses on the lead body, such as through providing a gradual transition from a non-squeezed section of the lead to the squeezed portion and back to non-squeezed portion.

In operation according to embodiments, locking of a slip ring anchor to a lead is independent of securing (e.g., by suturing) the slip ring anchor to the fascia or other tissue. Accordingly, the force used to secure the slip ring anchor to the lead is decoupled from the force used to secure the slip ring anchor to the fascia or other tissue, and a point of introducing potential for axial movement experienced by prior anchor configurations is avoided.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

DETAILED DESCRIPTION OF THE INVENTION

Figure 1A:
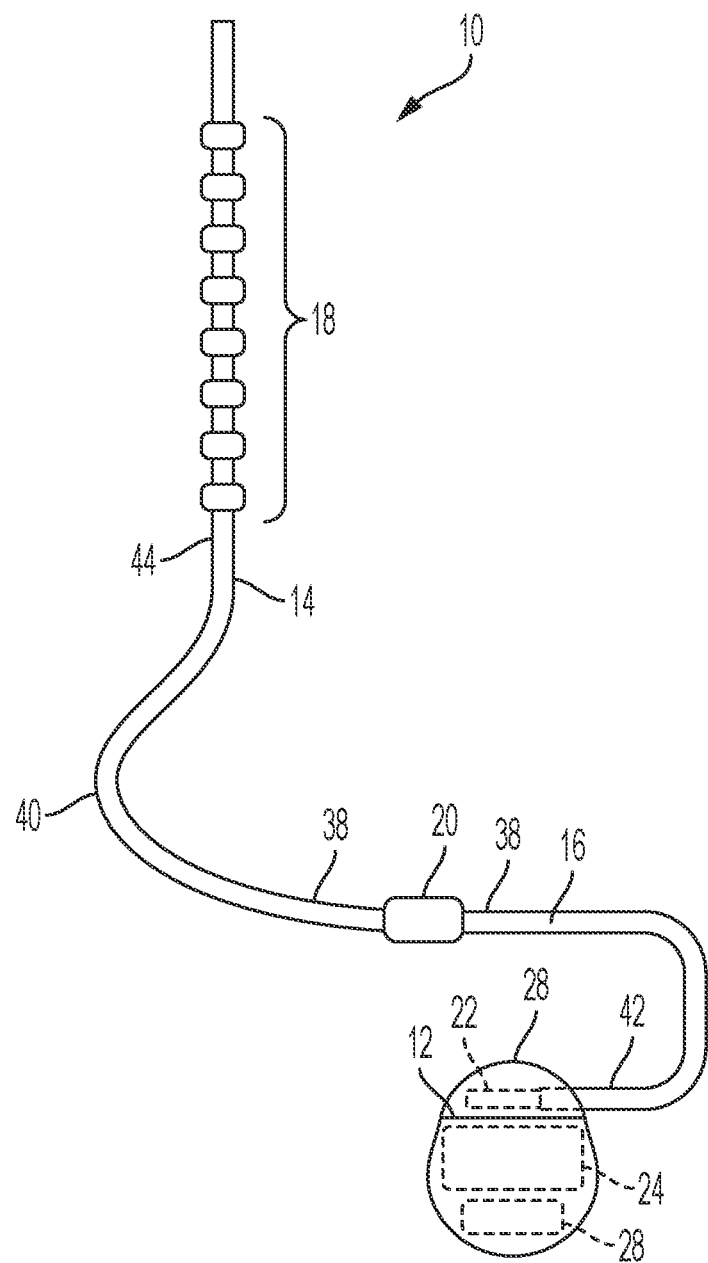
FIG. 1A shows a therapy delivery system as may utilize embodiments of a slip ring anchor of the present invention.

Slip ring anchor configurations are provided according to embodiments of the invention for use in anchoring or otherwise discouraging movement of medical device leads. For example, a slip ring anchor may be utilized with respect to a lead in the form of a catheter comprising part of an implantable medical device operable to deliver an infusate to a targeted tissue or treatment area. As another example, a slip ring anchor may be utilized with respect to a lead in the form of an electrical lead comprising part of an implantable medical device operable to deliver electrical pulses or signals to a targeted tissue or nerves.

To aid in understanding concepts herein, the description that follows describes examples relating to implantable medical devices of a spinal cord stimulation (SCS) system. However, it is to be understood that, while embodiments of a slip ring anchor are well suited for applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder subluxation, headache, etc.

Accordingly, a slip ring anchor may be utilized with one or more therapy delivery elements comprising an electrical lead including one or more electrodes to deliver pulses or signals to a respective target tissue site in a patient. Additionally or alternatively, a slip ring anchor may be utilized with one or more therapy delivery elements comprising an electrical lead including sensing electrodes to sense physiological parameters (e.g., blood pressure, temperature, cardiac activity, etc.) at a target tissue site within a patient.

In accordance with some embodiments, a slip ring anchor may be utilized with one or more therapy delivery elements comprising a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In the various embodiments contemplated by this disclosure, therapy may include stimulation therapy, sensing or monitoring of one or more physiological parameters, fluid delivery, and the like. A therapy delivery element (also referred to as a lead) may include pacing or defibrillation leads, stimulation leads, sensing leads, fluid delivery conduit, extensions for any of the above, or combinations thereof. A target tissue site may refer generally to the target site for implantation of a therapy delivery element, regardless of the type of therapy.

FIG. 1A illustrates a generalized therapy delivery system 10 that may be used in SCS, as well as other stimulation applications. Therapy delivery system 10 generally includes implantable pulse generator 12, implantable lead 14, which carries an array of electrodes 18 (shown exaggerated for purposes of illustration), and optional implantable extension lead 16. Although only one lead 14 is shown, typically two or more leads are used with the therapy delivery system 10 (e.g., as shown in FIG. 1C).

Lead 14 includes elongated body 40 having proximal end 36 and distal end 44. Elongated body 40 typically has a diameter of between about 0.03 inches to 0.07 inches and a length within the range of 30 cm to 90 cm for spinal cord stimulation applications. Elongated body 40 may be composed of a suitable electrically insulative material, such as a polymer (e.g., polyurethane or silicone), and may be extruded as a unibody construction.

In the illustrated embodiment, proximal end 36 of lead 14 is electrically coupled to distal end 38 of extension lead 16 via a connector 20, typically associated with the extension lead 16. Proximal end 42 of extension lead 16 is electrically coupled to implantable pulse generator 12 via connector assembly 22 associated with housing 28. Alternatively, proximal end 36 of lead 14 can be electrically coupled directly to connector 20.

In the illustrated embodiment, implantable pulse generator 12 includes electronic subassembly 24 (shown schematically), which includes control and pulse generation circuitry (not shown) for delivering electrical stimulation energy to electrodes 18 of lead 14 in a controlled manner. Implantable pulse generator 12 of the illustrated embodiment further includes a power supply, such as battery 26.

Implantable pulse generator 12 provides a programmable stimulation signal (e.g., in the form of electrical pulses or substantially continuous-time signals) that is delivered to target stimulation sites by electrodes 18. In applications with more than one lead 14, implantable pulse generator 12 may provide the same or a different signal to electrodes 18 of the therapy delivery elements.

In accordance with some embodiments, implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In still another embodiment, implantable pulse generator 12 can take the form of an external trial stimulator (ETS), which has similar pulse generation circuitry as an implantable pulse generator (IPG), but differs in that it is a non-implantable device that is used on a trial basis after lead 14 has been implanted and prior to implantation of the IPG, to test the responsiveness of the stimulation that is to be provided.

Housing 28 is composed of a biocompatible material, such as for example titanium, and forms a hermetically sealed compartment containing electronic subassembly 24 and battery 26 is protected from the body tissue and fluids. Connector assembly 22 is disposed in a portion of housing 28 that is, at least initially, not sealed. Connector assembly 22 carries a plurality of contacts that electrically couple with respective terminals at proximal ends of lead 14 or extension lead 16. Electrical conductors extend from connector assembly 22 and connect to electronic subassembly 24.

Figure 1B:
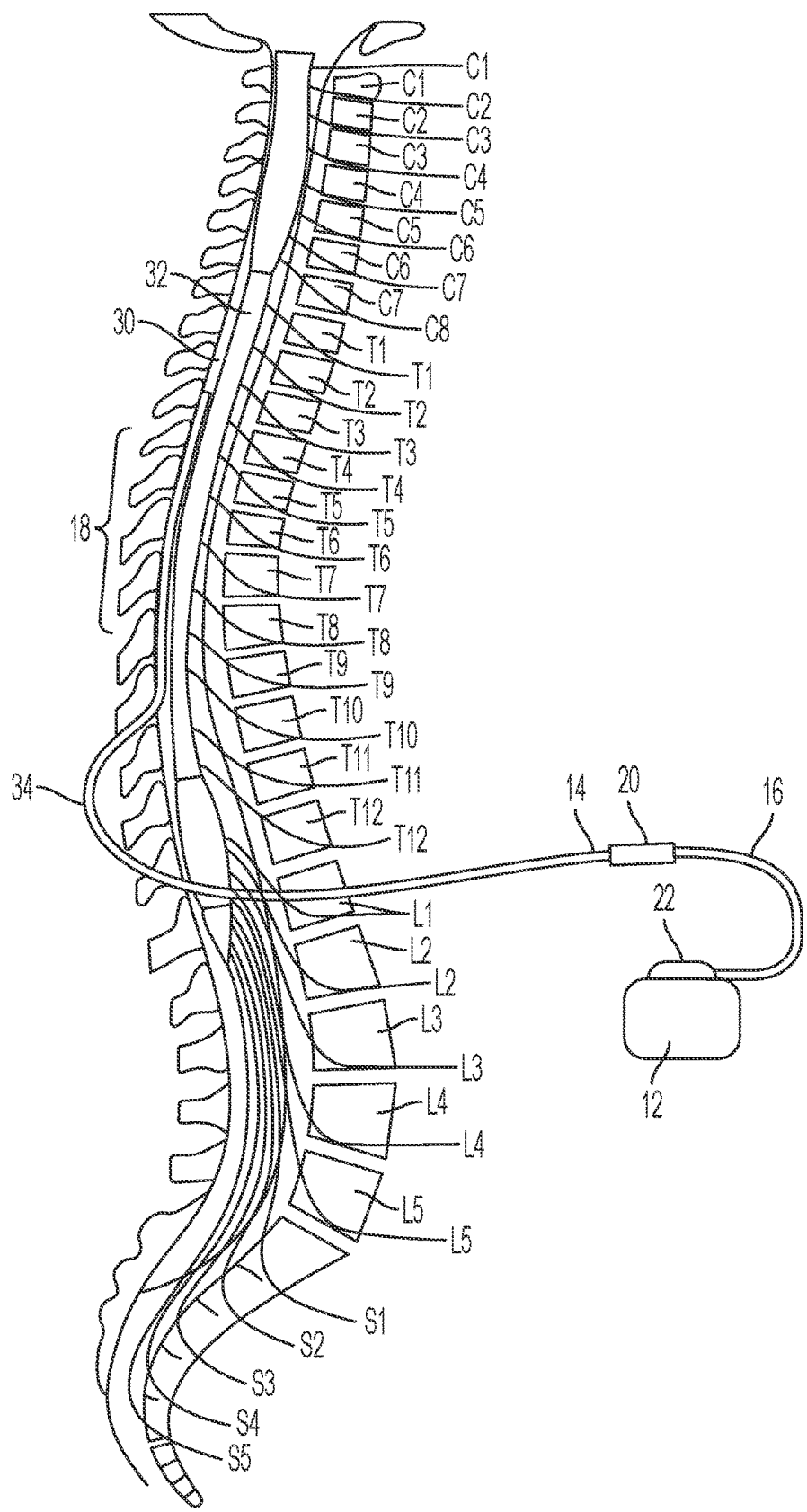
FIGS. 1B and 1C show an environment for a therapy delivery system in which a slip ring anchor of embodiments of the present invention may be deployed.
Figure 1C:
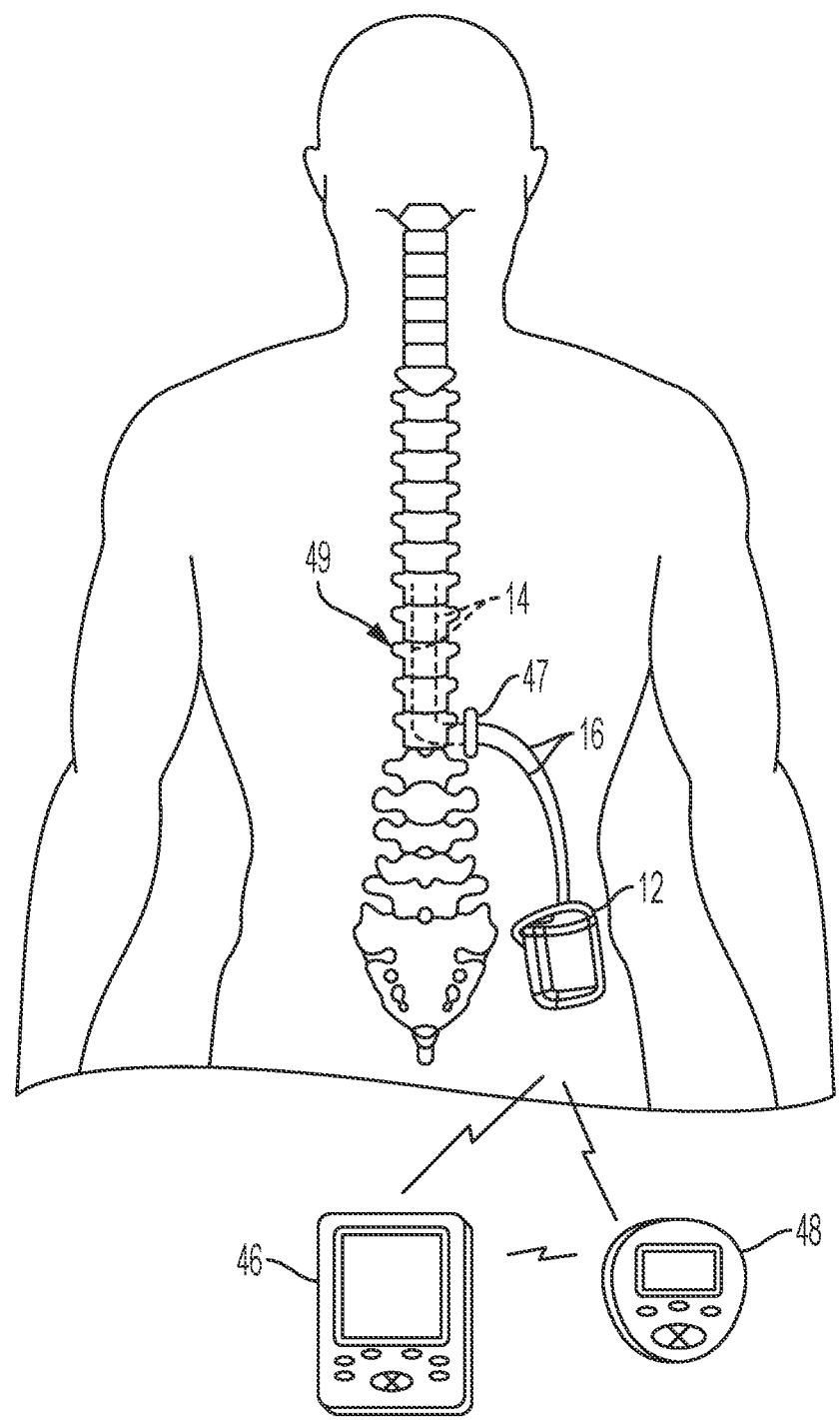

FIG. 1B illustrates lead 14 implanted in epidural space 30 of a patient in close proximity to the dura, the outer layer that surrounds spinal cord 32, to deliver the intended therapeutic effects of spinal cord electrical stimulation. The target stimulation sites may be anywhere along spinal cord 32. Such as for example proximate the sacral nerves.

Because of the lack of space near lead exit point 34 where lead 14 exits the spinal column, implantable pulse generator 12 is generally implanted in a surgically-made pocket either in the abdomen or above the buttocks, such as illustrated in FIG. 1C. Implantable pulse generator 12 may, of course, also be implanted in other locations of the patient's body. Use of extension lead 16 facilitates locating implantable pulse generator 12 away from lead exit point 34. In some embodiments, extension lead 16 serves as a lead adapter if proximal end 36 of lead 14 is not compatible with connector assembly 22 of implantable pulse generator 12, since different manufacturers use different connectors at the ends of their stimulation leads and are not always compatible with connector assembly 22.

As illustrated in FIG. 1C, therapy delivery system 10 also may include clinician programmer 46 and patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with implantable pulse generator 12 to download neurostimulation parameters and, optionally, upload operational or physiological data stored by implantable pulse generator 12. In this manner, the clinician may periodically interrogate implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and implantable pulse generator 12. Patient programmer 48 provides a patient with an interface for control of neurostimulation therapy provided by implantable pulse generator 12. For example, a patient may use patient programmer 48 to start, stop or adjust neurostimulation therapy. In particular, patient programmer 48 may permit a patient to adjust stimulation parameters such as duration, amplitude, pulse width and pulse rate, within an adjustment range specified by the clinician via clinician programmer 48, or select from a library of stored stimulation therapy programs.

Implantable pulse generator 12, clinician programmer 46, and patient programmer 48 may communicate via cables or a wireless communication. Clinician programmer 46 and patient programmer 48 may, for example, communicate via wireless communication with implantable pulse generator 12 using radio frequency (RF) telemetry techniques known in the art. Clinician programmer 46 and patient programmer 48 also may communicate with each other using any of a variety of local wireless communication techniques, such as RF communication according to the 802.11 or BLUETOOTH specification sets, infrared communication (e.g., according to the IrDA standard), or other standard or proprietary telemetry protocols.

Since implantable pulse generator 12 is located remotely from target location 49 for therapy, lead 14 and/or extension leads 16 is typically routed through a pathways subcutaneously formed along the torso of the patient to a subcutaneous pocket where implantable pulse generator 12 is located. As used hereinafter, "lead" and "lead extension" are used interchangeably, unless content clearly dictates otherwise.

Leads are typically fixed in place near the location selected by the clinician using one or more anchors 47, such as in the epidural space 30. Anchor 47 can be positioned on lead 14 in a wide variety of locations and orientations to accommodate individual anatomical differences and the preferences of the clinician. Anchor 47 may then be affixed to tissue using fasteners, such as for example, one or more sutures, staples, screws, or other fixation devices. The tissue to which anchor 47 is affixed may include subcutaneous fascia layer, bone, or some other type of tissue. Securing anchor 47 to tissue in this manner prevents or reduces the chance that lead 14 will become dislodged or will migrate in an undesired manner.

FIGS. 2A-2F and 3A-3E show example embodiments of slip ring anchor configurations according to concepts of the present disclosure. In particular, FIGS. 2A-2E show slip ring anchor 200 according to one exemplary embodiment and FIGS. 3A-3D show slip ring anchor 300 according to another exemplary embodiment. Slip ring anchors 200 and 300 may, for example, be utilized as anchor 47 of FIGS. 1A-1C.

The slip ring anchors of FIGS. 2A-2E and 3A-3D implement configurations in which an anchor body includes inelastic members and a fluted elastomeric casing operable in cooperation to impart a radial compressive force to a corresponding lead body, as discussed in further detail below. It should be understood that, although the examples of slip ring anchors 200 and 300 of FIGS. 2A-2E and FIGS. 3A-3D are provided to aid in understanding the present invention, the particular embodiments illustrated are exemplary and are non-limiting with respect to particular implementations encompassed by the concepts herein.

Referring first to the examples of FIGS. 2A-2F, slip ring anchor 200 of the illustrated embodiment includes anchor body 210 and slip rings 240 (shown as slip rings 240a and 240b). As will be understood from the disclosure below, slip ring anchor 200 is configured according to concepts herein to provide a tight friction interface between the anchor and a lead (e.g., lead 14) through cooperative operation of anchor body 210 and slip rings 240 locking the slip ring anchor to the lead.

Figure 2A:
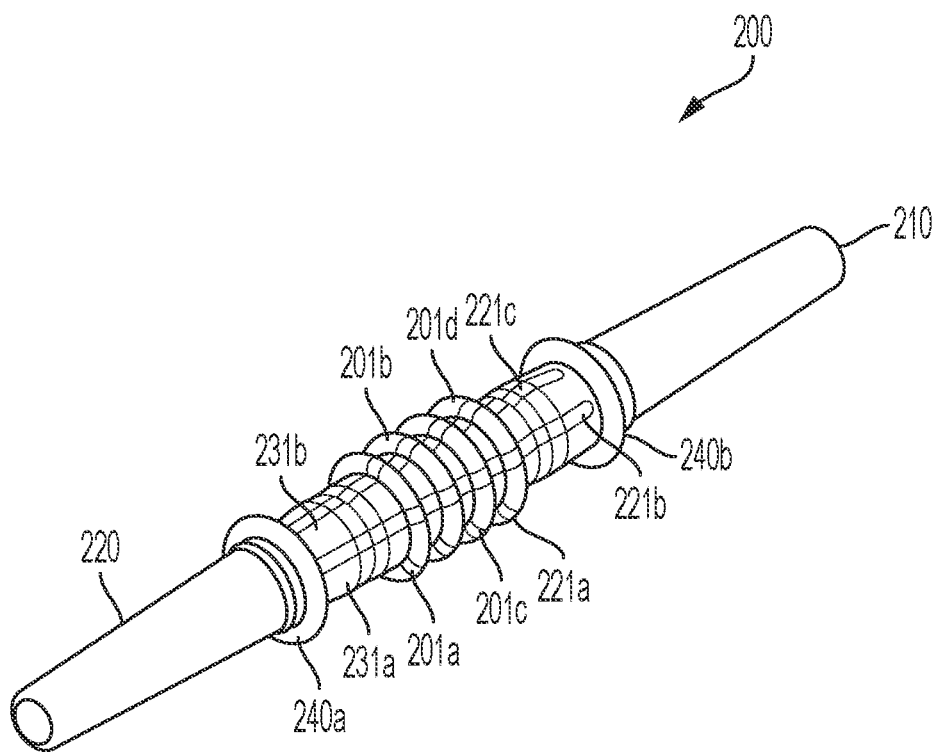
FIGS. 2A-2E show a slip ring anchor configuration of some embodiments of the present invention.
Figure 2B:
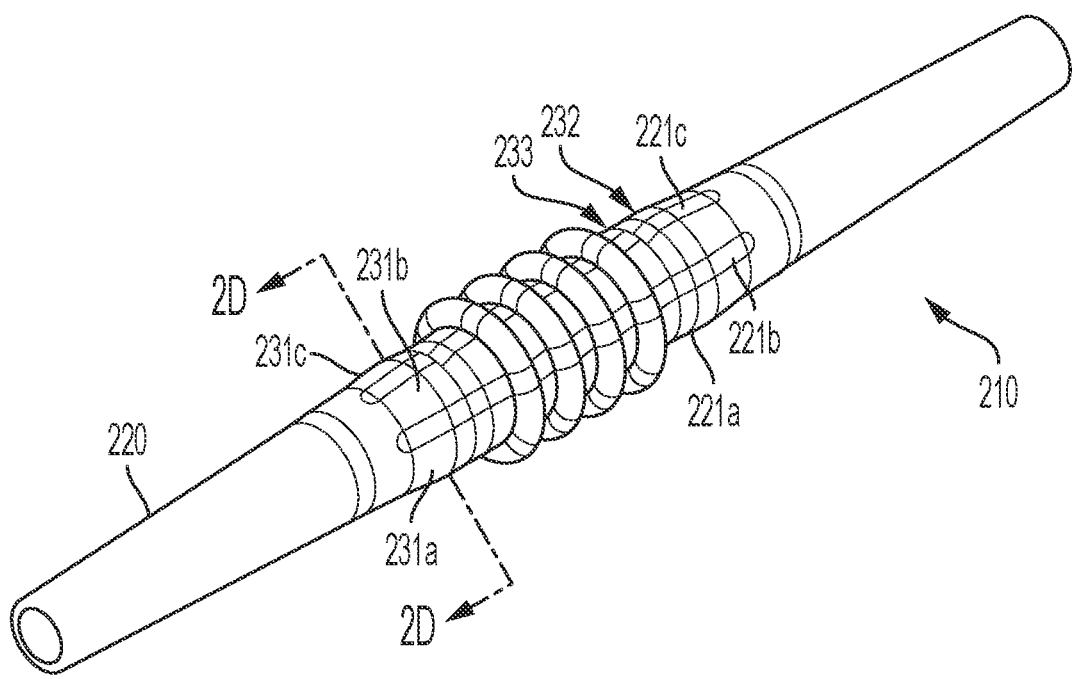
Figure 2C:
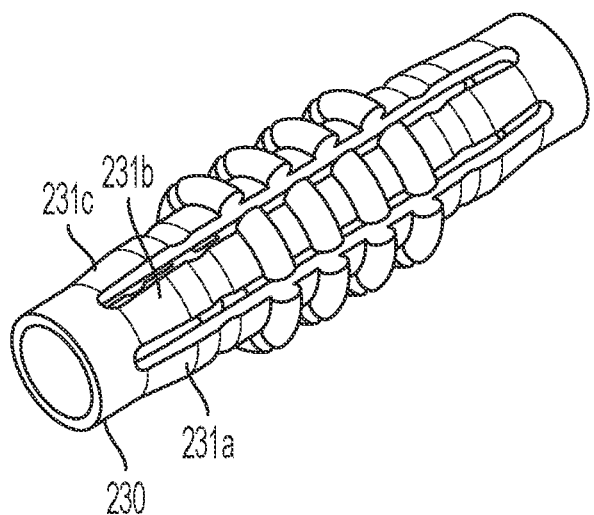
Figure 2D:
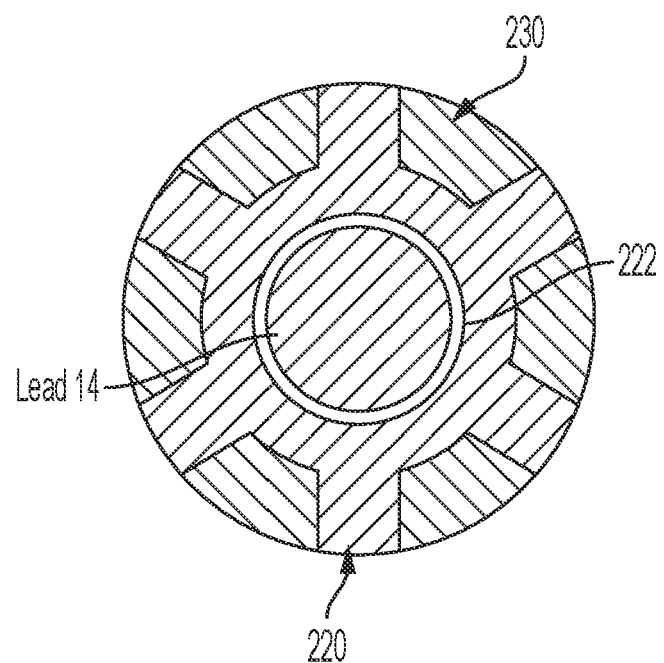

As shown in FIG. 2B, anchor body 210 may comprise fluted elastomeric casing 220 and a plurality of inelastic members 231 (inelastic members 231a-231c being visible in the illustration). Inelastic members 231 of embodiments comprise rigid or substantially rigid structures, such as may be made from various forms of hard plastics, polymers, etc. (e.g., thermoplastics, such as polyethylene, polypropylene, acrylonitrile butadiene styrene (ABS), polycarbonate, etc., and/or other relatively rigid biocompatible materials) that are resistant to compression and structural deformation under operational forces. Fluted elastomeric casing 220 of embodiments comprises a resilient or flexible structure, such as may be made from various forms of elastomeric material including flexible rubbers, polymers, etc. (e.g., polyurethane, silicone, synthetic rubber, etc., and/or other relatively compliant biocompatible materials) that are deformable under operational forces to impart radial compressive forces as described herein.

Inelastic members 231 of the illustrated embodiment of slip ring anchor 200 are disposed within the flutes of fluted elastomeric casing 220. For example, individual ones of inelastic members 231 (inelastic members 231a-231c being visible in the illustration) are alternately disposed in the flutes of fluted elastomeric casing 220 (e.g., interleaved between elastomeric members 221, elastomeric members 221a-221c being visible in the illustration) defining flutes of fluted elastomeric casing 220. Inelastic members 231 may, for example, comprise a part of an anchor body framework, such as inelastic frame 230 shown in FIG. 2C. In accordance with some examples, fluted elastomeric casing 220 may comprise a resilient material over-molded onto inelastic frame 230 so as to form anchor body 210 in which alternate radial layers of inelastic polymer (e.g., inelastic members 231) and elastomeric polymer (e.g., elastomeric members 221) are provided.

Anchor body 210 comprises a lumen through which a body of lead 14 may be inserted. For example, as shown in the cross section view of FIG. 2D, fluted elastomeric casing 220 may form anchor lumen 222 having an inner diameter sized to accommodate an outer diameter of lead 14 (e.g., the inner diameter of anchor lumen 222 may be equal to or slightly larger than an outer diameter of lead 14) to accommodate insertion of lead 14 into anchor body 210 and to allow anchor body 210 to be positioned at a desired axial position along lead 14. In accordance with some embodiments, the inner diameter of anchor lumen 222 may be slightly less than an outer diameter of lead 14, such as to provide a slight friction fit configured to retain the anchor in a desired placement along lead 14 during manipulation to lock the slip ring anchor to the lead.

One or more slip rings of embodiments of slip ring anchor 200 are configured to engage anchor body 210 to encourage a tight friction interface between slip ring anchor 200 and a lead disposed within anchor lumen 222. Accordingly, slip rings may be shaped to encircle anchor body 210 and sized to compress a portion of fluted elastomeric casing 220 and/or press inelastic members 231 together and reduce the inner diameter of anchor lumen 222 when one or more slip rings are disposed in an engaged positon on anchor body 210. Slip rings of embodiments of the invention may be made from various forms of hard plastics, polymers, etc. (e.g., thermoplastics, such as polyethylene, polypropylene, ABS, polycarbonate, etc.), various forms of flexible rubbers, polymers, etc. (e.g., polyurethane, silicone, synthetic rubber, etc.), and/or other biocompatible materials.

Figure 2E:
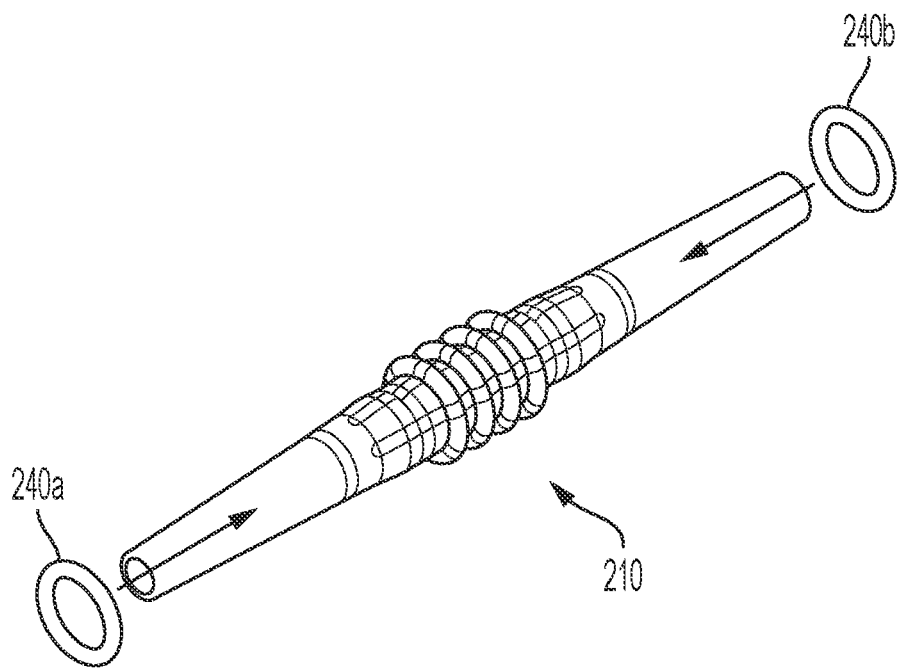
Figure 2F:
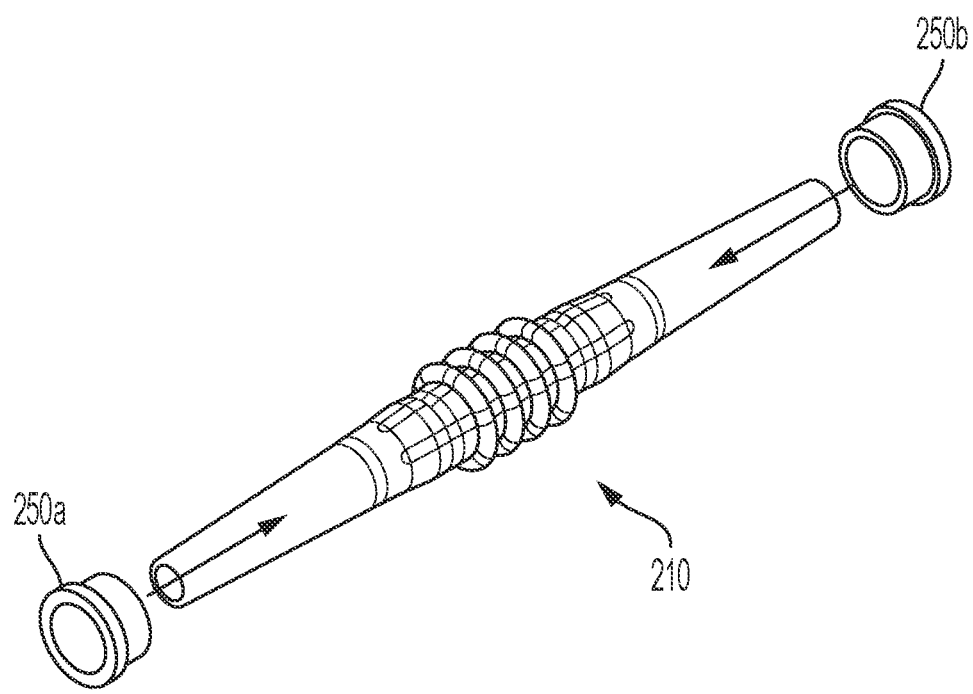
FIG. 2F shows an alternative slip ring configuration as may be used with a slip ring anchor of embodiments of the present invention.

The slip rings of embodiments of slip ring anchor 200 may be provided in a number of different form factors, such as the O-ring configuration of slip rings 240a and 240b shown in FIG. 2E or the sleeve configuration of slip rings 250a and 250b shown in FIG. 2F. For example, slip rings 240a and 240b may comprise rigid rings sized and shaped to correspond to anchor body 210. Similarly, slip rings 250a and 250b may comprise a rigid sleeve sized and shaped to correspond to anchor body 210.

In accordance with embodiments of the invention, one or more slip rings may be slipped over anchor body 210 (e.g., disposed in a disengaged position on anchor body 210) prior to insertion of a lead body into anchor lumen 222. For example, slip rings 240a and 240b may be slipped over anchor body 210 as shown in FIG. 2E to provide a completed slip ring anchor assembly (e.g., slip ring anchor 200 of FIG. 2A) ready for use with respect to lead 14. As another example, slip rings 250a and 250b may be slipped over anchor body 210 as shown in FIG. 2F to provide a completed slip ring anchor assembly ready for use with respect to lead 14.

Referring now to the example of FIGS. 3A-3E, slip ring anchor 300 of the illustrated embodiment includes anchor body 310 and slip ring 340. Similar to slip ring anchor 200 described above, slip ring anchor 300 is configured according to concepts herein to provide a tight friction interface between the anchor and a lead (e.g., lead 14) through cooperative operation of anchor body 310 and slip ring 340 locking the slip ring anchor to the lead.

Figure 3A:
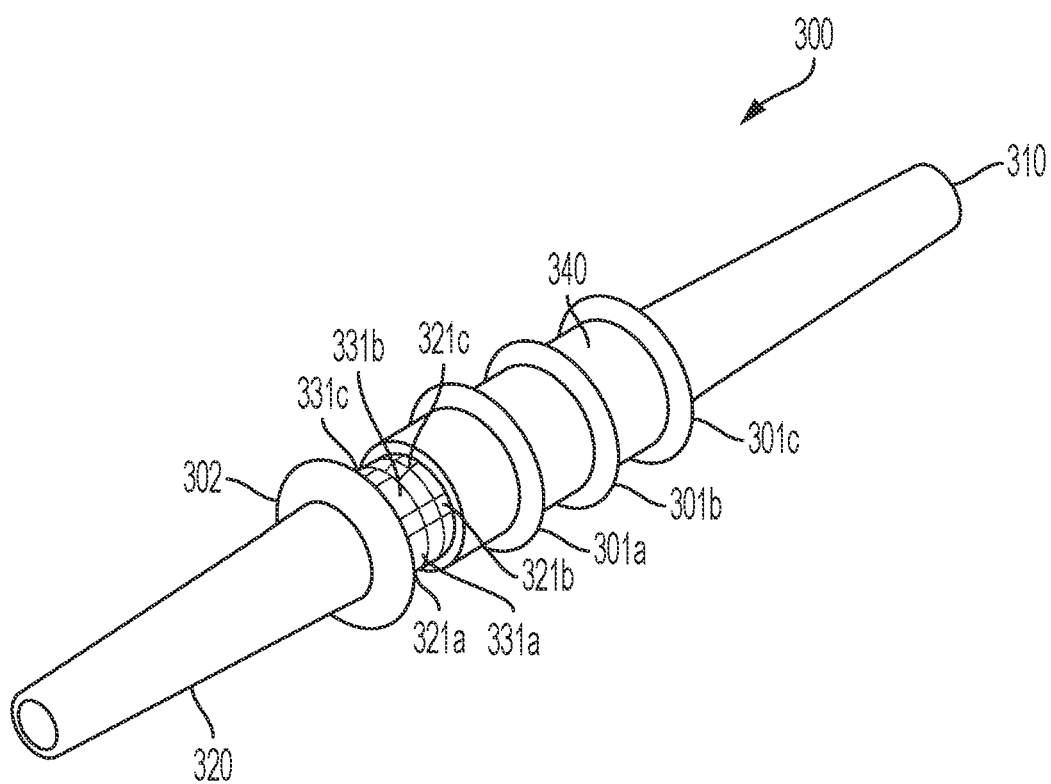
FIGS. 3A-3G show a slip ring anchor configuration of some additional embodiments of the present invention.
Figure 3B:
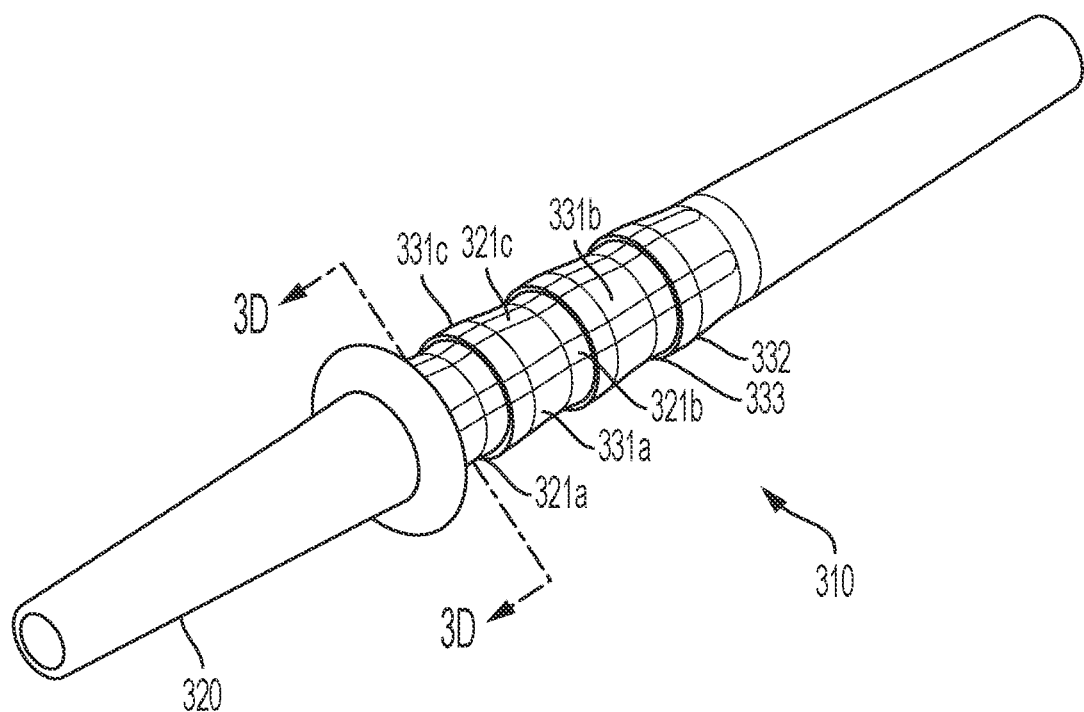
Figure 3C:
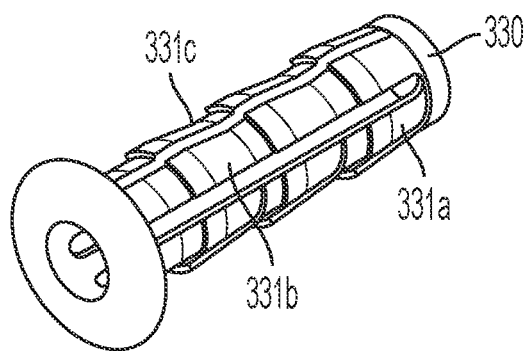
Figure 3D:
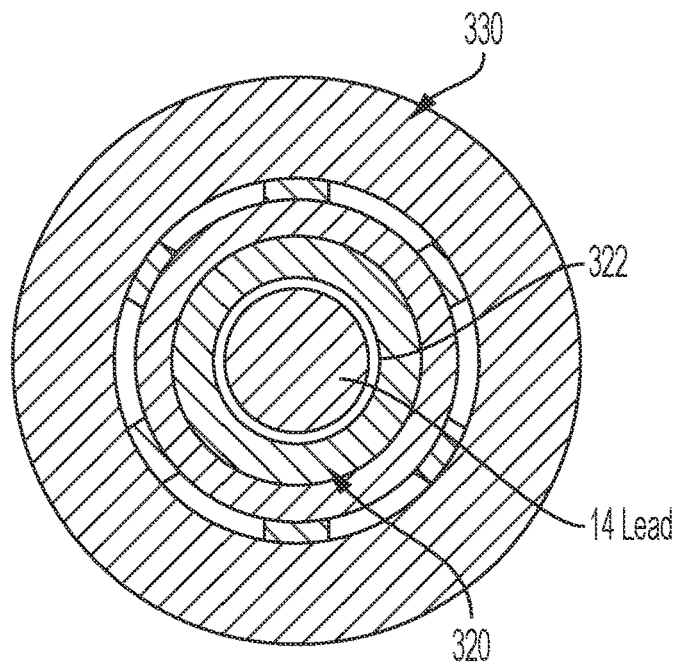

As shown in FIG. 3B, anchor body 310 may comprise fluted elastomeric casing 320 and a plurality of inelastic members 331 (inelastic members 331a-331c being visible in the illustration). As described above with respect to inelastic members 231, inelastic members 331 of embodiments comprise rigid or substantially rigid structures, such as may be made from various forms of hard plastics, polymers, etc. that are resistant to compression and structural deformation under operational forces. Further, as described above with respect to fluted elastomeric casing 220 above, fluted elastomeric casing 320 of embodiments comprises a resilient or flexible structure, such as may be made from various forms of elastomeric material including flexible rubbers, polymers, etc. that are deformable under operational forces to impart radial compressive forces as described herein.

Inelastic members 331 of the illustrated embodiment of slip ring anchor 300 are disposed within the flutes of fluted elastomeric casing 320. For example, individual ones of inelastic members 331 (inelastic members 331a-331c being visible in the illustration) are alternately disposed in the flutes of fluted elastomeric casing 310 (e.g., interleaved between elastomeric members 321, elastomeric members 321a-321c being visible in the illustration) defining flutes of fluted elastomeric casing 320. Inelastic members 331 may, for example, comprise a part of an anchor body framework, such as inelastic frame 330 shown in FIG. 3C. In accordance with some examples, fluted elastomeric casing 320 may comprise a resilient material over-molded onto inelastic frame 330 so as to form anchor body 310 in which alternate radial layers of inelastic polymer (e.g., inelastic members 331) and elastomeric polymer (e.g., elastomeric members 321) are provided.

Similar to anchor body 210, anchor body 310 comprises a lumen through which a body of lead 14 may be inserted. For example, as shown in the cross section view of FIG. 3D, fluted elastomeric casing 320 may form anchor lumen 322 having an inner diameter sized to accommodate an outer diameter of lead 14 (e.g., the inner diameter of anchor lumen 322 may be equal to or slightly larger than an outer diameter of lead 14) to accommodate insertion of lead 14 into anchor body 310 and to allow anchor body 310 to be positioned at a desired axial position along lead 14. In accordance with some embodiments, the inner diameter of anchor lumen 322 may be slightly less than an outer diameter of lead 14, such as to provide a slight friction fit configured to retain the anchor in a desired placement along lead 14 during manipulation to lock the slip ring anchor to the lead.

One or more slip rings of embodiments of slip ring anchor 300 are configured to engage anchor body 310 to encourage a tight friction interface between slip ring anchor 300 and a lead disposed within anchor lumen 322. Accordingly, slip rings may be shaped to encircle anchor body 310 and sized to compress a portion of fluted elastomeric casing 320 and/or press inelastic members 331 together and reduce the inner diameter of anchor lumen 322 when one or more slip rings are disposed in an engaged positon on anchor body 310. As described above, slip rings of embodiments may be made from various forms of hard plastics, polymers, etc., various forms of flexible rubbers, polymers, etc., and/or other biocompatible materials.

The slip ring of embodiments of slip ring anchor 300 may be provided in a number of different form factors. The illustrated example comprises a sleeve configuration of slip ring 340 shown in FIG. 3E. Slip ring 340 may, for example, comprise a rigid sleeve sized and shaped to correspond to anchor body 310. In another example, slip ring anchor 300 may comprise one or more slip rings comprising rigid rings sized and shaped to correspond to anchor body 310.

Figure 3E:
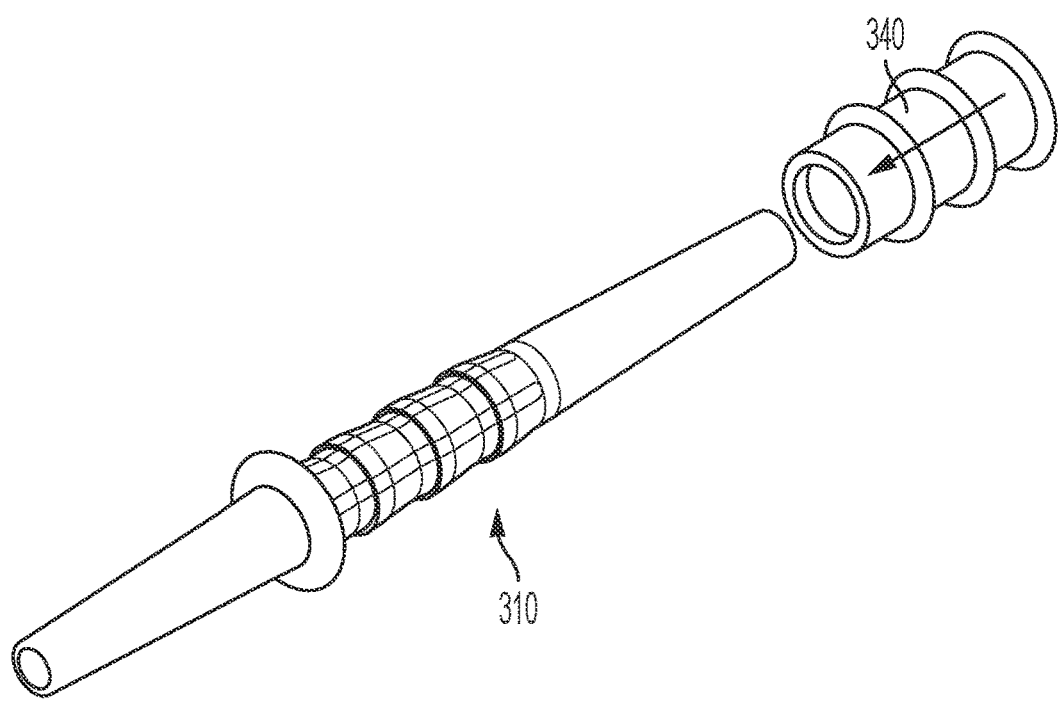

In accordance with embodiments of the invention, one or more slip rings may be slipped over anchor body 310 (e.g., disposed in a disengaged position on anchor body 310) prior to insertion of a lead body into anchor lumen 322. For example, slip ring 340 may be slipped over anchor body 310 as shown in FIG. 3E to provide a completed slip ring anchor assembly (e.g., slip ring anchor 300 of FIG. 3A) ready for use with respect to lead 14.

Figure 4A:
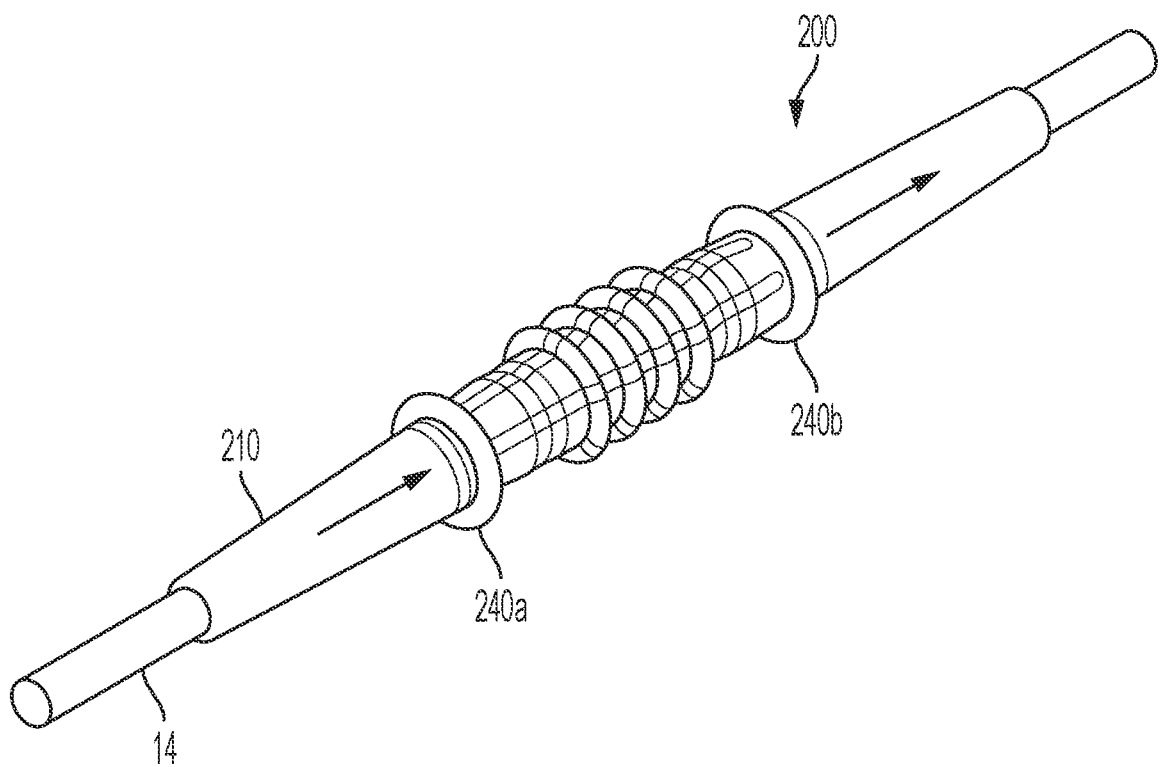
FIG. 4A illustrates a slip ring anchor of some embodiments of the present invention being positioned on a lead.
Figure 4B:
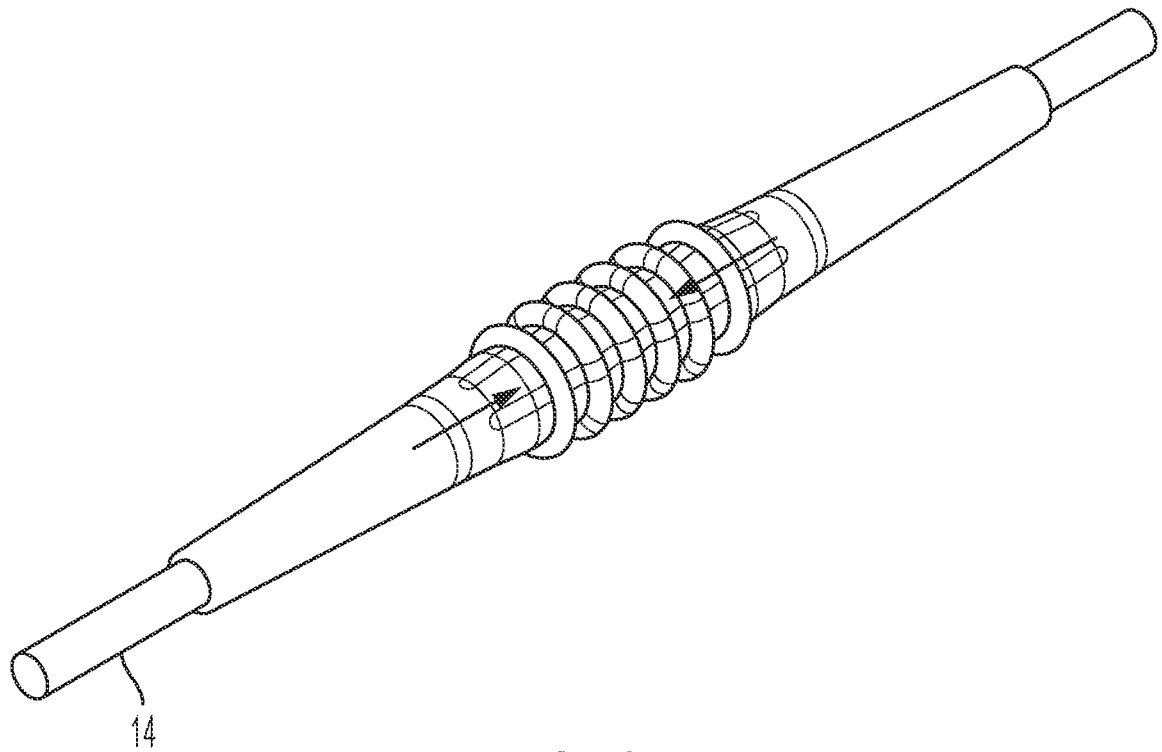
FIG. 4B illustrates a slip ring anchor of some embodiments of the present invention being affixed to a lead.
Figure 5A:
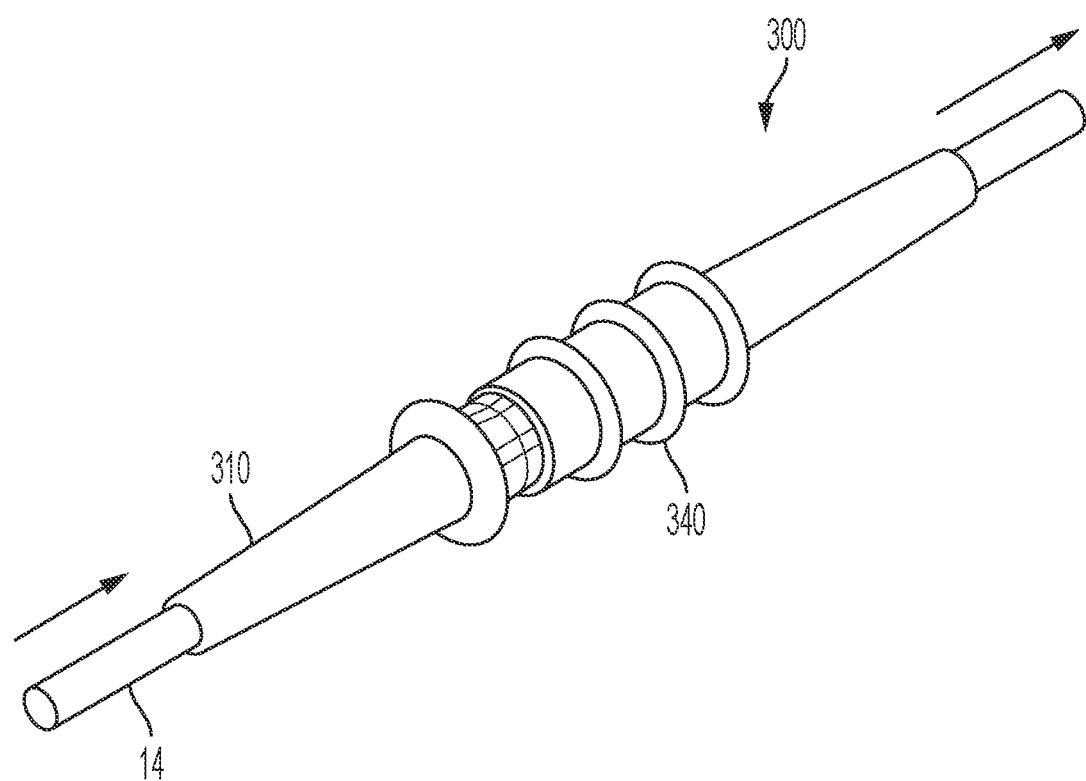
FIG. 5A illustrates a slip ring anchor of some additional embodiments of the present invention being positioned on a lead.
Figure 5B:
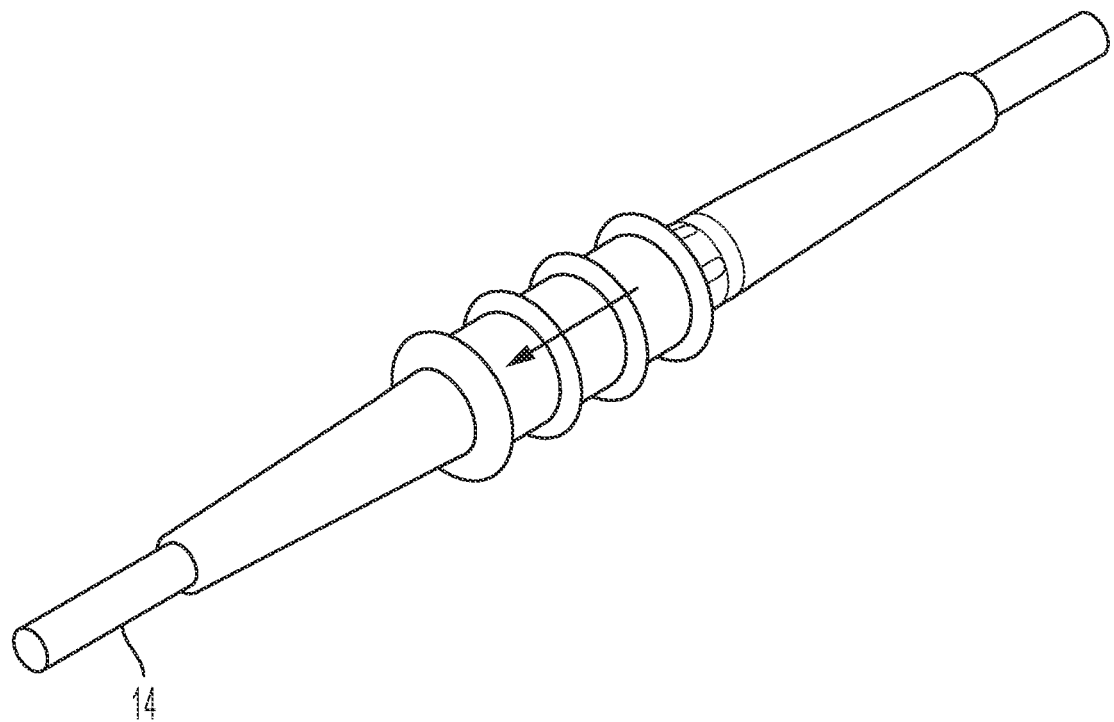
FIG. 5B illustrates a slip ring anchor of some additional embodiments of the present invention being affixed to a lead.

A lead (e.g., lead 14) may be inserted into the anchor lumen of a completed slip ring anchor assembly, whereby the slip ring anchor assembly may be moved axially along the lead to be positioned in a desired location with respect to the lead. For example, as shown in FIG. 4A, slip ring anchor 200 may be slid along lead 14 while slip rings 240a and 240b are disposed in disengaged positions on anchor body 210. Similarly, as shown in FIG. 5A, slip ring anchor 300 may be slid along lead 14 while slip ring 340 is disposed in disengaged positions on anchor body 310. After the slip ring anchor is suitably positioned axially on the lead, one or more slip ring may be manipulated to an engaged position with respect to the anchor body, as shown in FIG. 4B (slip ring anchor 200) and FIG. 5B (slip ring anchor 300), such as to facilitate holding the relative position of the slip ring anchor with respect to the lead. For example, manipulation of one or more slip rings may be used to cause a sufficient radial compressive force to be imparted upon the lead body by the slip ring anchor to hold the axial position of the slip ring anchor on the lead.

Figure 6A:
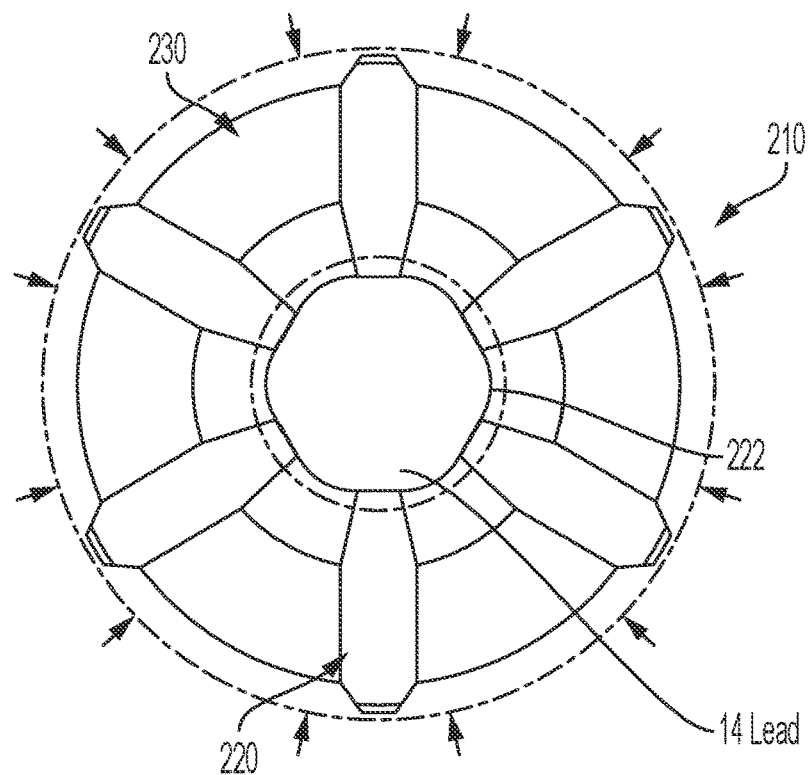
FIGS. 6A and 6B illustrate compression of a fluted elastomeric casing imparting a radial compressive force upon a portion of a lead when a respective slip ring is disposed in an engaged position with respect to the anchor body of embodiments of a slip ring anchor.

Slip rings of embodiments are configured to cooperate with the anchor body of a slip ring anchor and cause a radial compressive force to be imparted upon a lead body passed through the anchor lumen by the anchor body when the slip ring is in an engaged position. In operation of slip ring anchors of embodiments of the invention, the anchor body may be squeezed on the outside diameter by several methods (e.g., using slip rings in the form of O-rings, sleeves, etc.) that in turn reduce the inner diameter of the anchor lumen, and thus tighten the slip ring anchor on a lead. For example, embodiments of slip rings 240a and 240b of an embodiment may comprise rigid rings sized and shaped to correspond to anchor body 210. Accordingly, slip rings 240a and 240b may be configured to compress fluted elastomeric casing 220 of anchor body 210 (e.g., pressing inelastic members 231 together circumferentially) and encourage the fluted elastomeric casing to impart a radial compressive force upon a portion of lead 14 disposed in anchor lumen 222 when a respective slip ring is disposed in an engaged position with respect to the anchor body, as shown in FIG. 6A. Similarly, slip ring 340 of an embodiment may comprise a rigid sleeve sized and shaped to correspond to anchor body 310. Slip ring 340 may thus be configured to compress fluted elastomeric casing 320 of anchor body 310 (e.g., pressing inelastic members 331 together circumferentially) and encourage the fluted elastomeric casing to impart a radial compressive force upon a portion of lead 14 disposed in anchor lumen 322 when a respective slip ring is disposed in an engaged position with respect to the anchor body, as shown in FIG. 6B.

Figure 3F:
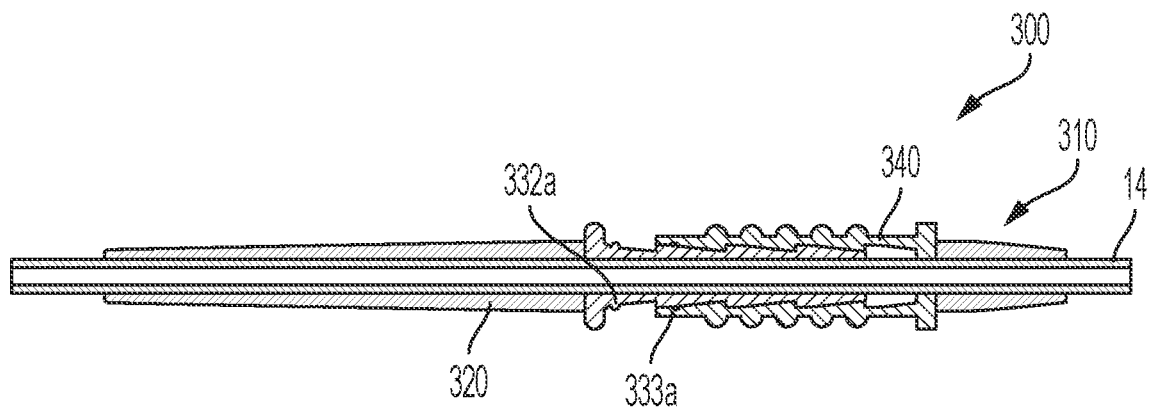
Figure 3G:
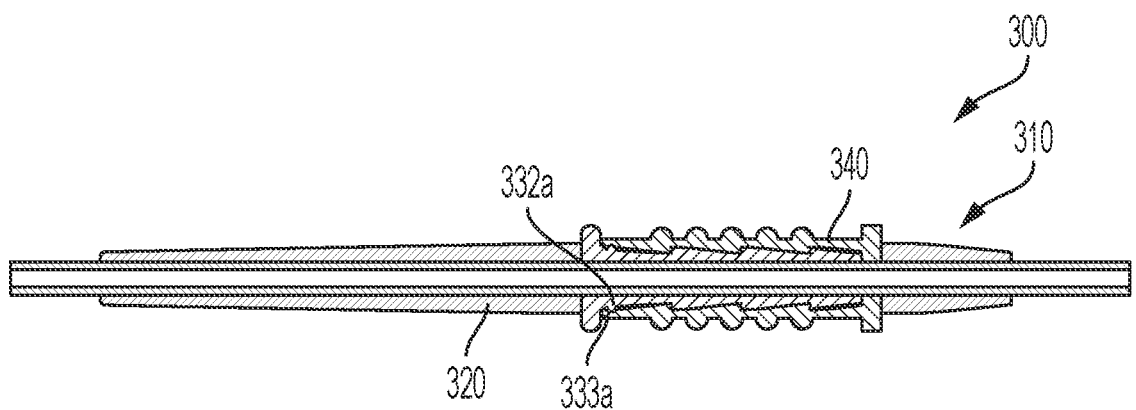

Anchor bodies of embodiments may include a slip ring engagement profile configured to operatively engage one or more slip rings, encourage compression of the fluted elastomeric casing, and provide a tight friction interface between the slip ring anchor and a lead disposed within the anchor lumen. Additionally or alternatively, a slip ring engagement profile of embodiments may be configured to retain a slip ring in an engaged position, such as to maintain compression of the fluted elastomeric casing indefinitely. For example, a slip ring engagement profile may include one or more shoulders (e.g., annular shoulder 232 shown in FIG. 2A, annular shoulder 332 shown in FIG. 3B, etc.) and/or one or more grooves (e.g., annular groove 233 shown in FIG. 2A, annular groove 333 shown in FIG. 3B, etc.) configured to retain a slip ring in an engaged position while inducing compression of the fluted elastomeric casing. It should be appreciated that features for retaining a slip ring in an engaged position may be provided in alternative configurations to those of FIGS. 2A and 3B discussed above. For example, FIGS. 3F and 3E illustrate a configuration in which shoulder 332a is provided by elastomeric casing 320 and shoulder 333a is provided by slip ring 340. Irrespective of their particular configuration, shoulders and corresponding grooves provided according to embodiments of the invention are sized, shaped, and positioned so as to engage one another when the slip ring is in an engaged (e.g. "locked") position with respect to the anchor body of a slip ring anchor. Further, structure provided to retain a slip ring in an engaged position may be provided in other than shoulder and groove configurations (e.g., pawl and latch detent, threaded interface, etc.).

Figure 6B:
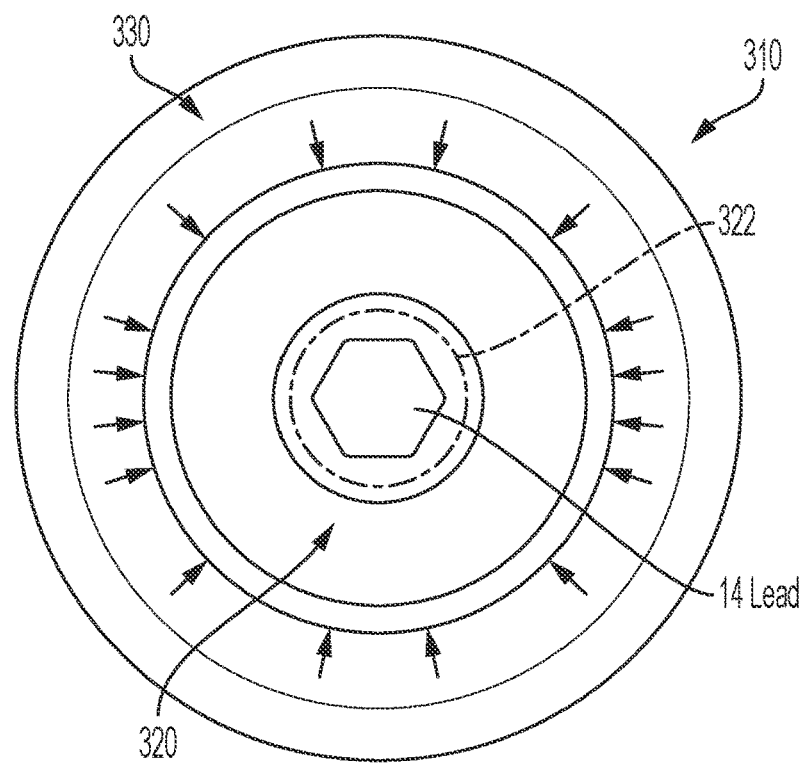

As can be seen in the illustrations of FIGS. 6A and 6B, a portion of fluted elastomeric casing may be squeezed by a slip ring to deform the elastomeric material resulting in a reduced inner diameter of the anchor lumen, and affixing the slip ring anchor on a lead. The inelastic members of the anchor body of embodiments resist compression, and may not significantly deform in response to a slip ring disposed in an engaged position. For example, although an inelastic member may flex slightly toward the anchor lumen, or otherwise be somewhat displaced, inelastic members of embodiments of the invention substantially retain their size and shape. Accordingly, the plurality of inelastic members interleaved in the flutes of the fluted elastomeric casing of embodiments are configured to restrict or control compression of the fluted elastomeric casing. For example, the number, size, shape, spacing, etc. of inelastic members provided with respect to a fluted elastomeric casing may be selected so as to control the radial compressive force imparted to the portion of the lead body by the anchor body. Further, in accordance with embodiments herein, the plurality of inelastic members interleaved in the flutes of a fluted elastomeric casing facilitates a substantially equal distribution of the radial compressive force around the portion of the lead body engaged by the slip ring anchor. Additionally or alternatively, the elastomeric material of a fluted elastomeric casing provided in association with inelastic members may be configured to restrict or control compression of the anchor body. For example, the amount, extent to which areas between inelastic members are filled, shape, etc. of elastomeric material forming a fluted elastomeric casing, or some portion thereof, may be selected so as to control the radial compressive force imparted to the portion of the lead body by the anchor body.

Embodiments of a slip ring anchor body have been described as comprising a plurality of inelastic members disposed a fluted elastomeric casing that forms an anchor lumen through which a lead body may be inserted. It should be appreciated, however, that variations on the particular examples described may be implemented according to concepts of the present invention. For example, elastomeric material may be disposed within areas (e.g., slots) between inelastic members of a slip ring anchor body without extending to an inner area of the slip ring anchor body. In some embodiments, a surface of the anchor lumen may be formed from the inner surfaces of the inelastic members and inner surfaces of elastomeric material disposed between, rather than an anchor lumen formed from a unitary surface of elastomeric material. In another example, elastomeric material may not extend longitudinally beyond a length of either or both ends of inelastic members of an anchor lumen. In some embodiments, elastomeric material may extend longitudinally for the length of the areas (e.g., slots) between the inelastic members of a slip ring anchor body (e.g., elastomeric material forming a fluted elastomeric casing, elastomeric material disposed in the areas between inelastic members without extending to an inner area of the slip ring anchor body, etc.). Elastomeric material of a slip ring anchor body of some embodiments may not fully fill areas between inelastic members according to some embodiments. For example, elastomeric material may not fill the areas (e.g., slots) between the inelastic members to the full outward radial size (height) of the inelastic members, to the full inward radial size (depths) of the inelastic members, and/or to the full longitudinal size (length) of the slots between the inelastic members. According to some embodiments, elastomeric material may be provided at the ends of the inelastic members without extending into, or substantially into, the areas (e.g., slots) between the inelastic members. For example, elastomeric material may be disposed at the ends of a plurality of inelastic members to hold the inelastic members in an orientation to define an anchor lumen and to allow radial compression of the arrangement of inelastic members by one or more slip rings.

In accordance with some examples, elastomeric material of anchor body implementations may be configured to facilitate uniform or improved distribution of gripping forces over a surface area of the lead body. For example, the amount and disposition of elastomeric material within areas between inelastic members and/or the location and extent of interfacing between elastomeric material and inelastic members may be configured to encourage equal radial compressive forces imparted by the inelastic members to a lead, avoiding or minimizing damage to the lead associated with sharp or sheer forces. Additionally or alternatively, elastomeric material of anchor body implementations may be configured to increase the grip on a lead by the slip ring anchor. For example, elastomeric material of embodiments may be over-molded on the radially inner surface of the inelastic members, such as to take up any inconsistencies, perturbations, or features in or on the surface of the lead. Such elastomeric material may conform to features (e.g., irregularities, detents, burrs, etc.) on the lead surface to facilitate an excellent gripping interface between the anchor body and the lead.

As can be appreciated by the foregoing, slip ring anchors of embodiments of the present invention may be utilized to provide a tight friction interface between the slip ring anchor and a lead without introducing sharp concentrated shear forces on the lead. For example, an anchor body implementing a fluted elastomeric casing and inelastic members alternately disposed in the flutes according to concepts herein may distribute compressive forces substantially equally around the lead body, such as by the slip ring anchor squeezing relatively consistently 360° around a portion of the anchor comprising the fluted elastomeric casing with alternately disposed inelastic members compressed by a slip ring. Further, an anchor body implementing a fluted elastomeric casing and inelastic members alternately disposed in the flutes according to concepts herein may avoid sharp shear stresses on the lead body, such as through providing a gradual transition from a non-squeezed section of the lead to the squeezed portion and back to non-squeezed portion.

One or more structures providing various functionality may be provided with respect to an anchor body and/or slip ring of configurations of a slip ring anchor of embodiments. For example, in addition to being configured to engage a lead body so as to maintain a relative position axially with respect to the lead, slip ring anchors of embodiments of the invention may be configured for affixing to surrounding tissue of a patient within which the lead is disposed. Slip ring anchors 200 and 300 may, for example, be affixed to tissue using various forms of fasteners (e.g., sutures, staples, screws, and/or other fixation devices). Accordingly, anchor bodies and/or slip rings of embodiments of the invention may comprise one or more structures to assist affixing of the slip ring anchor to tissue of the patient. For example, one or more rib structures, such as ribs 201a-201d shown on anchor body 210 in FIG. 2A and/or ribs 301a-301c shown on slip ring 340 in FIG. 3A, may be provided for use in affixing the slip ring anchor to tissue. Additionally or alternatively, one or more anchor loops (not shown) or other similar structures may be provided on anchor bodies and/or slip rings of embodiments of slip ring anchors.

In some examples, one or more structures may be provided to facilitate manipulation of a slip ring into or out of an engaged positon on the anchor body of a slip ring anchor. For example, ribs 201a-201d and ribs 301a-301c may, in addition to being configured for use in affixing the slip ring anchor to tissue, be configured for manipulation of a corresponding slip ring between engaged and disengaged positions. A slip ring actuator tool of embodiments may be used to manipulate a slip ring between disengaged (e.g., "unlocked") and engaged (e.g. "locked") positions with respect to a slip ring anchor, such as for affixing the slip ring anchor at a desired position on a lead body through application of a radial compressive force, disengaging the radial compressive force for removal or repositioning of the slip ring anchor, etc. One or more of ribs 201a-201d and ribs 301a-301c may be configured for use with respect to such a slip ring actuator tool, such as in combination with cooperative structure of the slip ring anchor.

Figure 7A:
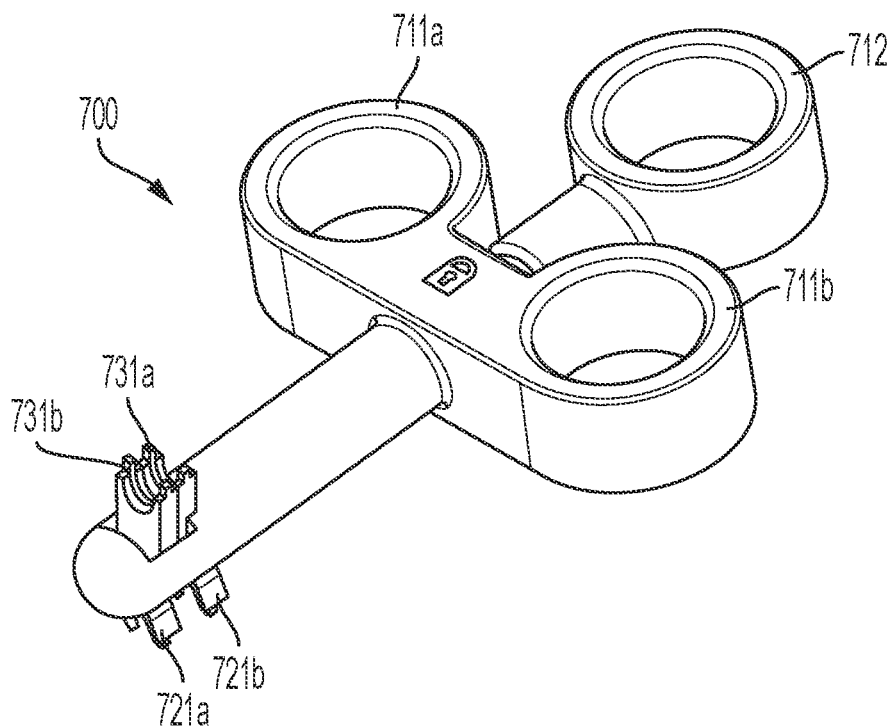
FIGS. 7A, 7B, 8A, 8B, 9A, 9B, 10A, and 10B, show a slip ring actuator tool configuration of some embodiments of the present invention.
Figure 7B:
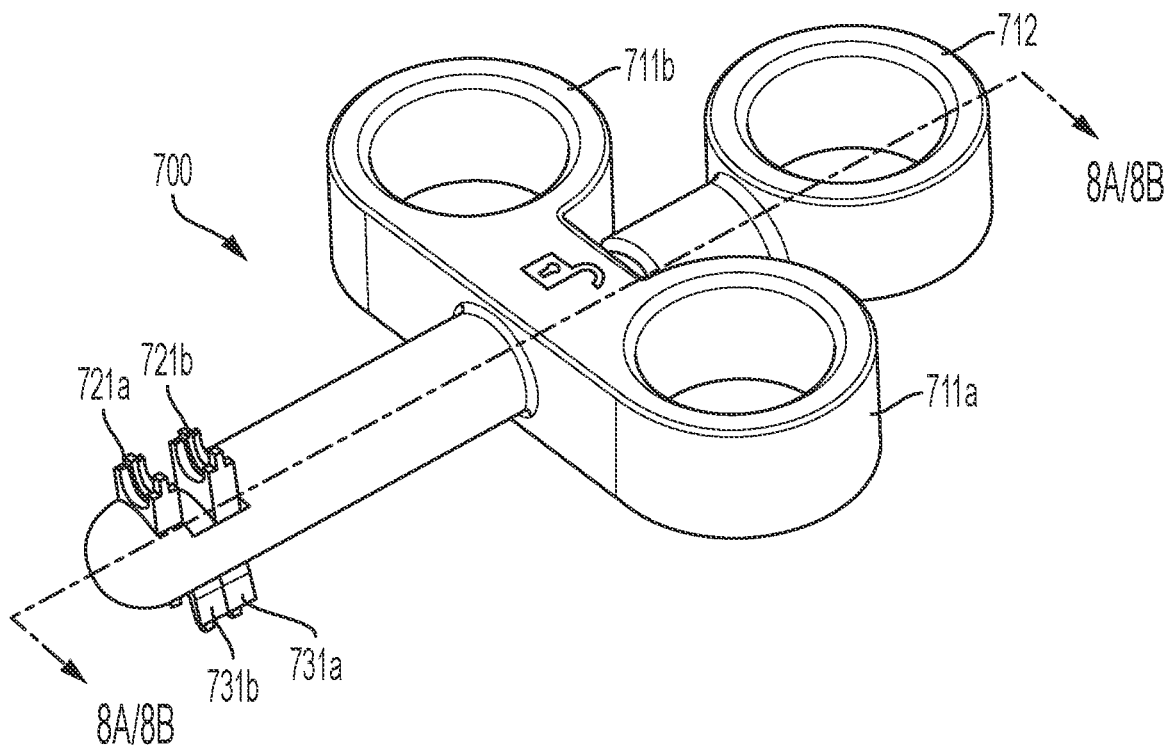

FIGS. 7A and 7B show an example embodiment of a slip ring actuator tool. In particular, FIG. 7A shows slip ring actuator tool 700 from a first side, the orientation of which may be used for manipulating a slip ring into an engaged or "locked" position according to embodiments. Correspondingly, FIG. 7B shows slip ring actuator tool 700 from a second side, the orientation of which may be used for manipulating a slip ring out of an engaged position to an "unlocked" position (e.g., disengaged) according to embodiments.

Slip ring actuator tool 700 of the illustrated embodiment includes finger grips 711a and 711b and thumb grip 712 configured for manual operation of the slip ring actuator tool, such as by a physician implanting a lead upon which a slip ring anchor of embodiments of the present invention is disposed. Alternative embodiments of a slip ring actuator tool may comprise automated means for operation, such as through use of one or more servos, linear actuators, pistons, etc.

Irrespective of the particular form of locomotion implemented for its operation, slip ring actuator tool 700 of the illustrated example utilizes slip ring manipulation interface members (referred to as manipulation shoes herein). In the illustrated example, slip ring actuator tool 700 includes locking manipulation shoes 721a and 721b operable cooperatively for manipulating a slip ring into an engaged or "locked" position. Further, slip ring actuator tool 700 of the illustrated example includes unlocking manipulation shoes 731a and 732b operable cooperatively for manipulating a slip ring into a disengaged or "unlocked" position. The manipulation shoes of embodiments of slip ring actuator tool 700 may be configured to interface with structure of a slip ring actuator (e.g., a slip ring, rib structures, etc.) for application of a locking and/or unlocking manipulation force. In accordance with some embodiments, manipulations shoes of a slip ring actuator tool may have a profile to substantially conform to surface shapes of corresponding structure of a slip ring anchor for facilitating application of locking and/or unlocking manipulation force.

Figure 8A:
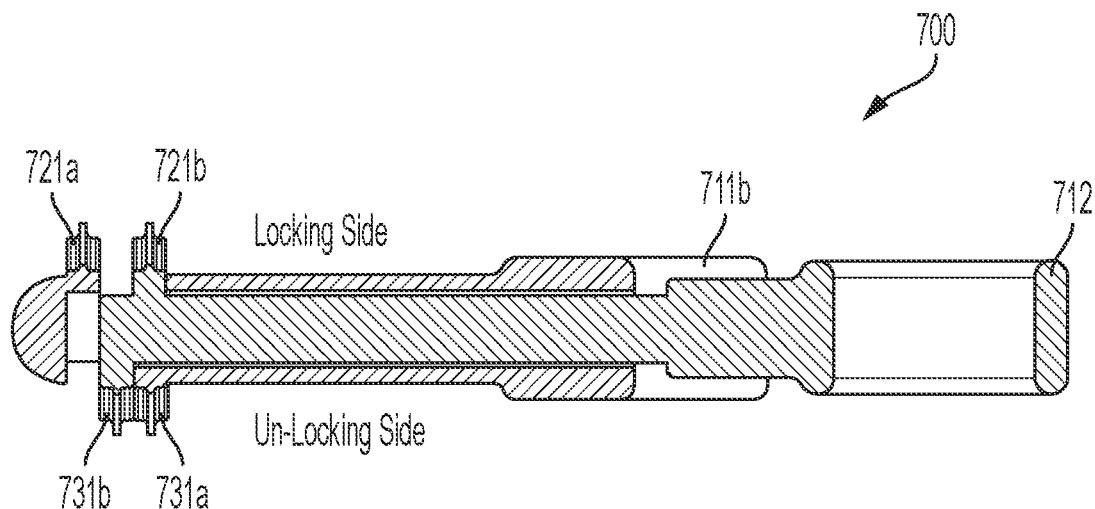
Figure 8B:
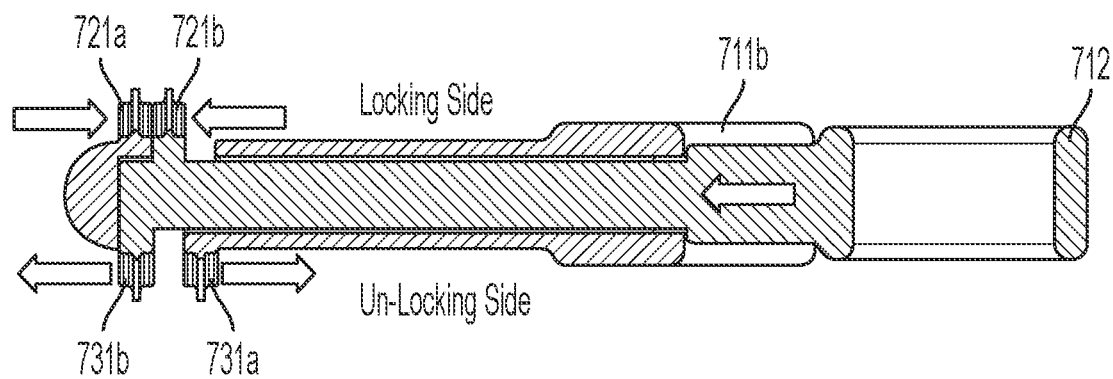

The cross section views of FIGS. 8A and 8B illustrate operation of slip ring actuator tool 700. As shown in FIG. 8A, when slip ring actuator tool 700 is at rest (e.g., thumb grip 712 has not been depressed with respect to finger grips 711a and 711b), locking manipulation shoes 721a and 721b are disposed in an open or separated configuration whereas unlocking manipulation shoes 731a and 731b are disposed in a closed or non-separated configuration. As shown in FIG. 8B, when slip ring actuator tool 700 is operated (e.g., thumb grip 712 is depressed with respect to finger grips 711a and 711b), locking manipulation shoes 721a and 721b are moved to a closed or non-separated configuration whereas unlocking manipulation shoes 731a and 731b are moved to an open or separated configuration. This operation may be used to facilitate manipulation of a slip ring into or out of an engaged positon on the anchor body of a slip ring anchor.

Figure 9A:
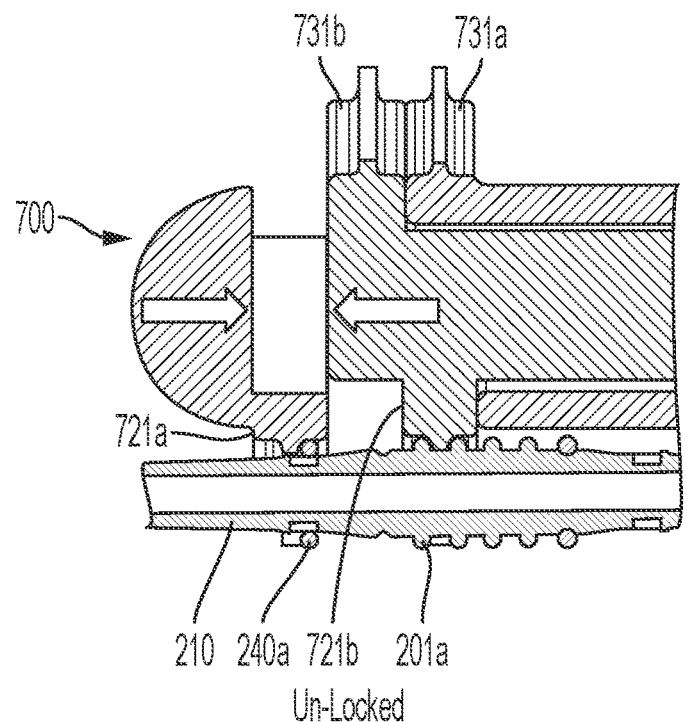
Figure 9B:
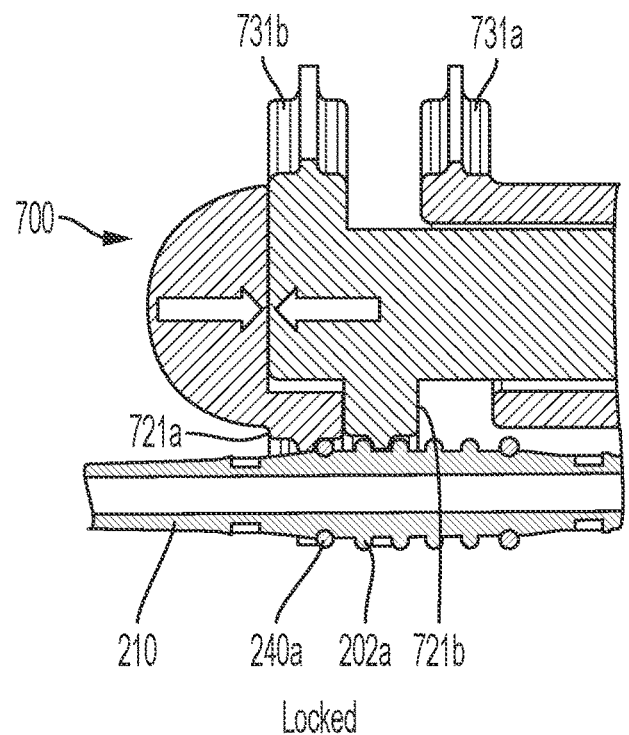

FIGS. 9A and 9B illustrate operation of slip ring actuator tool 700 providing manipulation of slip ring 240a into an engaged positon on anchor body 210 of slip ring anchor 200. In the illustrated example, slip ring actuator tool 700 in a resting configuration (e.g., thumb grip 712 has not been depressed with respect to finger grips 711a and 711b) is positioned as shown in FIG. 9A such that locking manipulation shoe 721a interfaces with slip ring 240a disposed in a disengaged position on anchor body 210 and such that locking manipulation shoe 721b interfaces with rib 201a. Thereafter, slip ring actuator tool 700 may be operated (e.g., thumb grip 712 is depressed with respect to finger grips 711a and 711b) as shown in FIG. 9B such that locking manipulation shoes 721a and 721b move from an open or separated configuration to a closed or non-separated configuration. Through such operation of slip ring actuator tool 700, slip ring 240a is encouraged to move from a disengaged position to an engaged position with respect to anchor body 210 in light of rib 201a having a fixed position upon the anchor body and the relative movement of locking manipulation shoe 721a.

Figure 10A:
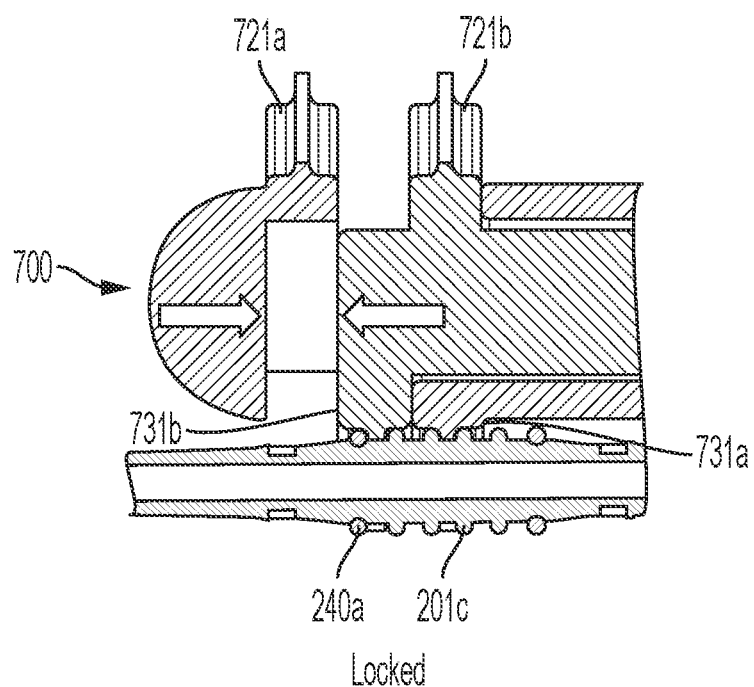
Figure 10B:
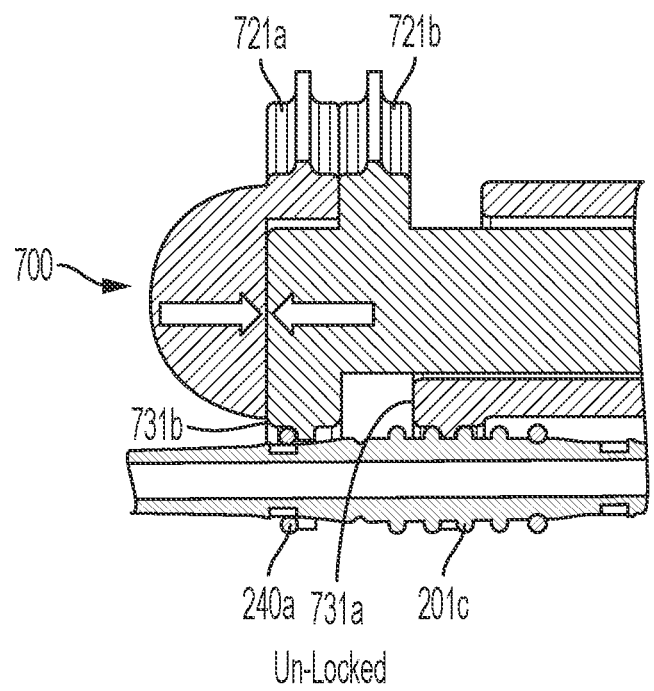

FIGS. 10A and 10B illustrate operation of slip ring actuator tool 700 providing manipulation of slip ring 240a from an engaged positon to a disengaged position on anchor body 210 of slip ring anchor 200. In the illustrated example, slip ring actuator tool 700 in a resting configuration (e.g., thumb grip 712 has not been depressed with respect to finger grips 711a and 711b) is positioned as shown in FIG. 10A such that locking manipulation shoe 731b interfaces with slip ring 240a disposed in an engaged position on anchor body 210 and such that locking manipulation shoe 731a interfaces with rib 201c. Thereafter, slip ring actuator tool 700 may be operated (e.g., thumb grip 712 is depressed with respect to finger grips 711a and 711b) as shown in FIG. 10B such that locking manipulation shoes 731a and 731b move from a closed or non-separated configuration to an open or separated configuration. Through such operation of slip ring actuator tool 700, slip ring 240a is encouraged to move from an engaged position to a disengaged position with respect to anchor body 210 in light of rib 201c having a fixed position upon the anchor body and the relative movement of locking manipulation shoe 731b.

As illustrated by FIGS. 9A, 9B, 10A, and 10B, a slip ring actuator tool of embodiments may be used to lock and/or unlock a slip ring anchor on a lead. For example, by moving the one or more slip rings of a slip ring anchor between engaged or locked positions and disengaged or unlocked positions on the anchor body, the anchor may be positioned on the lead, locked, unlocked, repositioned on the lead, and relocked. It should be appreciated, however, that slip rings of embodiments of a slip ring anchor need not be repositioned upon the anchor body for unlocking a slip ring anchor with respect to the lead. For example, a slip ring (e.g., an O-ring configuration of slip ring) may be cut and discarded to remove the slip ring anchor.

As can be appreciated from the foregoing, locking of a slip ring anchor to a lead according to embodiments may be performed independent of securing (e.g., by suturing) the slip ring anchor to the fascia or other tissue. Accordingly, the force used to secure the slip ring anchor to the lead is decoupled from the force used to secure the slip ring anchor to the fascia or other tissue, and a point of introducing potential for axial movement experienced by prior anchor configurations is avoided.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. An anchor system for use with respect to a medical device lead, the anchor system comprising:
    an anchor body having a plurality of inelastic members and an elastomeric material forming an anchor lumen configured for insertion of a lead body therein, wherein the elastomeric material comprises a fluted elastomeric casing forming the anchor lumen, wherein inelastic members of the plurality of inelastic members are disposed within alternate flutes of the fluted elastomeric casing to provide the plurality of inelastic members in an interleaved configuration with the alternate flutes of the fluted elastomeric casing, and wherein the plurality of inelastic members and the elastomeric material are configured to cooperate to impart a radial compressive force to the lead body; and
    one or more slip rings configured to encircle the plurality of inelastic members and cause the radial compressive force to be imparted upon the lead body by the anchor body.

2. The anchor system of claim 1, wherein the elastomeric material comprises a material over-molded on the plurality of inelastic members.

3. The anchor system of claim 1, wherein the elastomeric material is disposed within areas between inelastic members of the plurality of inelastic members.

4. The anchor system of claim 3, wherein the elastomeric material fills less than a complete volume of space in the areas between the inelastic members.

5. The anchor system of claim 3, wherein a surface of the anchor lumen is formed from inner surfaces of the inelastic members and inner surfaces of the elastomeric material disposed between the inelastic members.

6. The anchor system of claim 3, wherein the one or more slip rings are configured to compress the fluted elastomeric casing and encourage the fluted elastomeric casing to impart the radial compressive force upon a portion of the lead body disposed in the anchor lumen when the one or more slip rings are disposed engaged positions with respect to the anchor body.

7. The anchor system of claim 3, wherein the plurality of inelastic members are configured to restrict compression of the elastomeric material and control the radial compressive force imparted to a portion of the lead body by the anchor body.

8. The anchor system of claim 1, wherein the radial compressive force is distributed substantially equally around the portion of the lead body.

9. The anchor system of claim 1, wherein the anchor body comprises a slip ring engagement profile configured to operatively engage the one or more slip rings and encourage the radial compressive force.

10. The anchor system or claim 9, wherein the slip ring engagement profile is configured to retain the one or more slip rings in relative positions axially along the anchor body to maintain the radial compressive force imparted upon the lead body.

11. The anchor system of claim 10, wherein the slip ring engagement profile includes one or more shoulders configured to retain each of the one or more slip rings in an engaged position while inducing the radial compressive force.

12. The anchor system of claim 1, wherein the one or more slip rings comprise a sleeve configured to compress the elastomeric material.

13. The anchor system of claim 12, wherein the one or more slip rings comprise one or more annular rings disposed on the sleeve.

14. The anchor system of claim 1, wherein the medical device lead comprises an electrical lead for an implantable medical device.

15. The anchor system of claim 1, wherein the medical device lead comprises a catheter for an implantable medical device.

16. The anchor system of claim 1, further comprising:
    a slip ring actuator tool configured to manipulate the one or more slip rings between disengaged and engaged positions with respect to the anchor body.

17. A method for affixing an anchor to a medical device lead, the method comprising:

disposing an anchor body at a desired axial position along a body of the medical device lead, wherein the anchor body includes a plurality of inelastic members and an elastomeric material forming an anchor lumen configured for insertion of the body of the medical device lead therein, wherein the elastomeric material comprises a fluted elastomeric casing forming the anchor lumen, wherein inelastic members of the plurality of inelastic members are disposed within alternate flutes of the fluted elastomeric casing to provide the plurality of inelastic members in an interleaved configuration with the alternate flutes of the fluted elastomeric casing, and, and the plurality of inelastic members and the elastomeric material are configured to cooperate to impart a radial compressive force to the body of the medical device lead; and manipulating a slip ring encircling the anchor body to an engaged position with respect to the anchor body, wherein the slip ring is configured to cooperate with the anchor body and cause the radial compressive force to be imparted upon the body of the medical device lead by the anchor body when the slip ring is in the engaged position.

18. The method of claim 17, wherein the fluted elastomeric casing comprises a material over-molded on the plurality of inelastic members.

19. The method of claim 18, wherein the elastomeric material is disposed within areas between inelastic members of the plurality of inelastic members.

20. The method of claim 19, wherein the elastomeric material fills less than a complete volume of space in the areas between the inelastic members.

21. The method of claim 19, wherein a surface of the anchor lumen is formed from inner surfaces of the inelastic members and inner surfaces of the elastomeric material disposed between the inelastic members.

22. The method of claim 19, wherein the slip ring is configured to compress the fluted elastomeric casing and encourage the fluted elastomeric casing to impart the radial compressive force upon a portion of the lead body disposed in the anchor lumen when the slip ring is disposed in the engaged position.

23. The method of claim 22, wherein the plurality of inelastic members are configured to restrict compression of the fluted elastomeric casing and control the radial compressive force imparted to the portion of the lead body by the anchor body.

24. The method of claim 17, wherein the radial compressive force is distributed substantially equally around the portion of the lead body.

25. The method of claim 17, wherein the anchor body comprises a slip ring engagement profile configured to operatively engage the slip ring and encourage the radial compressive force.

26. The method of claim 25, wherein the slip ring engagement profile is configured to retain the slip ring in a relative position axially along the anchor body to maintain the radial compressive force imparted upon the lead body.

27. The method of claim 26, wherein the slip ring engagement profile includes one or more shoulders configured to retain the slip ring in the engaged position while inducing the radial compressive force.

28. The method of claim 17, wherein the slip ring comprises a sleeve configured to compress the elastomeric material.

29. The method of claim 28, wherein the slip ring comprises one or more annular rings disposed on the sleeve.

30. The method of claim 17, wherein the medical device lead comprises an electrical lead for an implantable medical device.

31. The method of claim 17, wherein the medical device lead comprises a catheter for an implantable medical device.

32. The method of claim 17, further comprising:
interfacing a slip ring actuator tool with the slip ring to manipulate the slip ring between a disengaged position and the engaged position.

33. An anchor system for use with respect to a medical device lead, the anchor system comprising:
an anchor body having a plurality of inelastic members and a fluted elastomeric casing forming an anchor lumen configured for insertion of a lead body therein, wherein inelastic members of the plurality of inelastic members are disposed within alternate flutes of the fluted elastomeric casing to provide the plurality of inelastic members in an interleaved configuration with the flutes of the fluted elastomeric casing; and
one or more slip rings configured to encircle the plurality of inelastic members and the fluted elastomeric casing and cause a radial compressive force to be imparted upon the lead body by the anchor body, wherein the one or more slip rings comprise a sleeve configured to compress the fluted elastomeric casing and encourage the fluted elastomeric casing to impart the radial compressive force upon a portion of the lead body disposed in the anchor lumen when the one or more slip rings are disposed engaged positions with respect to the anchor body, and wherein the plurality of inelastic members are configured to restrict compression of the fluted elastomeric casing and control the radial compressive force to be imparted substantially equally around the portion of the lead body by the anchor body.

34. The anchor system of claim 33, wherein the fluted elastomeric casing comprises a material over-molded on the plurality of inelastic members.

35. The anchor system of claim 33, wherein the anchor body comprises a slip ring engagement profile configured to operatively engage the one or more slip rings and encourage compression of the fluted elastomeric casing and to retain the one or more slip rings in relative positions axially along the anchor body.

36. The anchor system of claim 33, further comprising:
a slip ring actuator tool configured to manipulate the one or more slip rings between disengaged and engaged positions with respect to the anchor body.

* * * * *